(12) United States Patent
Nagakawa et al.

(10) Patent No.: US 8,574,896 B2
(45) Date of Patent: Nov. 5, 2013

(54) COLORIMETRIC METHOD AND REAGENT USED FOR THE SAME

(75) Inventors: Kenji Nagakawa, Kyoto (JP); Tomomichi Tsujimoto, Kyoto (JP); Susumu Nishino, Kyoto (JP); Masaaki Teramoto, Kyoto (JP); Yoshiyuki Kawase, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 715 days.

(21) Appl. No.: 12/469,403

(22) Filed: May 20, 2009

(65) Prior Publication Data

US 2009/0233322 A1 Sep. 17, 2009

Related U.S. Application Data

(62) Division of application No. 10/476,298, filed as application No. PCT/JP03/00027 on Jan. 6, 2003, now Pat. No. 7,550,273.

(30) Foreign Application Priority Data

Dec. 28, 2001 (JP) ................................ 2001-400380

(51) Int. Cl.
*C12M 1/34* (2006.01)

(52) U.S. Cl.
USPC ..................................... 435/288.7; 435/287.1

(58) Field of Classification Search
USPC .......................................... 435/287.1, 288.7
See application file for complete search history.

(56) References Cited

U.S. PATENT DOCUMENTS

| 4,233,402 | A | 11/1980 | Maggio et al. |
| 4,701,420 | A | 10/1987 | Thunberg et al. |
| 5,036,000 | A | 7/1991 | Palmer et al. |
| 5,410,059 | A | 4/1995 | Fraser et al. |
| 5,418,142 | A | 5/1995 | Kiser et al. |
| 5,434,055 | A | 7/1995 | Jernigan |
| 5,938,917 | A | 8/1999 | Mulchandani |
| 6,140,294 | A | 10/2000 | Delroisse et al. |
| 2005/0014213 | A1 | 1/2005 | Nagakawa et al. |

FOREIGN PATENT DOCUMENTS

| EP | 0 100 217 | 2/1984 |
| EP | 0 513 594 | 11/1992 |
| EP | 1 457 572 | 9/2004 |
| EP | 1 466 987 | 10/2004 |
| JP | 57-192483 | 11/1982 |
| JP | 1-155244 | 6/1989 |
| JP | 3-43096 | 2/1991 |
| JP | 10-253633 | 9/1998 |
| WO | 92/15701 | 9/1992 |
| WO | 94/17199 | 8/1994 |
| WO | 96/25514 | 8/1996 |
| WO | 99/17115 | 4/1999 |
| WO | 01/21827 | 3/2001 |

OTHER PUBLICATIONS

Schryvers et al. "The anaerobic sn-glycerol-3-phosphate dehydrogenase of *Escherichia coli*", JBC, 1981, 256(19):9959-9965.*
Kimura et al. "Further studies on superoxide dismutase activities of macrocyclic polyamine complexes of copper (II)", Biochimica et Biophysica Acta, 1983, 745:37-43.*
Oyama et al. "Catalysis of the electroreduction of hydrogen peroxide by montmorillonite clay coatings of graphite electrodes", J. Electroanal. Chem. 1986, 199:467-470.*
Eguchi et al. "The aerobic reduction of Fe(III) complexes by hemoglobin and myoglobin", The Journal of Biological Chemistry, 1984, 259(23):14337-14338.*
Kosela, et al., "Charge mediation by ruthenium poly(pyridine) complexes in 'second-generation' glucose biosensors based on carboxymethylated β-cyclodextrin polymer membranes", Anal Bioanal Chem (2002) 373: 724-734.
Zaitoun, "A Kinetic-Spectrophotometric Method for Determination of Glucose in Solutions", Journal of Analytical Chemistry, 2006, vol. 61, No. 10, pp. 1010-1014.
Birk, et al., "Mechanism of the Reduction of Bromate Ion by Cyano(bipyridyl)iron(II) Complexes", Inorganic Chemistry, vol. 17, No. 5, 1978.
Oyama, et al., "Catalysis of the Electroreduction of Hydrogen Peroxide by Montmorillonite Clay Coatings on Graphite Electrodes", J. Electronanal. Chem., 199 (1986) 467-470.

* cited by examiner

*Primary Examiner* — Bin Shen
(74) *Attorney, Agent, or Firm* — Morgan, Lewis & Bockius LLP

(57) ABSTRACT

The present invention provides a colorimetric method that can perform a simple and reliable analysis in a short time. The method includes transferring an electron from an analyte to a coloring reagent that produces color by reduction via a mediator by using an oxidoreductase; and performing qualitative or quantitative analysis of the analyte by measuring color produced in the coloring reagent. The enzyme reaction of this method is a single stage reaction, and the color production reaction occurs via the mediator. Therefore, the measurement can be performed in a short time. Since this reaction requires neither hydrogen peroxide nor oxygen, the measured values are highly reliable.

12 Claims, 11 Drawing Sheets

COLORIMETRIC METHOD AND REAGENT USED FOR THE SAME

CROSS REFERENCE TO RELATED APPLICATIONS

This application is a Division of application Ser. No. 10/476,298, filed Dec. 11, 2003, which is a U.S. National Stage of PCT/JP03/00027, filed Jan. 6, 2003, which applications are incorporated herein by reference.

TECHNICAL FIELD

The present invention relates to a calorimetric method and a reagent used for the same.

BACKGROUND ART

In the field of clinical or biochemical examinations, a calorimetric analysis is employed as a method for analyzing components such as glucose, cholesterol, or the like in a sample. For example, the colorimetric analysis of glucose is generally as follows: a glucose oxidase reacts with glucose (substrate) to generate gluconolactone and hydrogen peroxide; and the hydrogen peroxide is detected by a coloring reagent, such as a Trinder's reagent, in the presence of peroxidase. This method, in which the concentration of a substrate is measured indirectly via hydrogen peroxide, has been limited not only to glucose, but also used for cholesterol or the like.

However, the conventional calorimetric analysis involves the following problems. First, the time required for measurement is long because an analyte is not measured directly, but indirectly via hydrogen peroxide. For example, it takes 30 to 60 seconds to measure glucose. Second, it is difficult to set conditions because two different enzyme reaction systems should be stabilized simultaneously. Finally, the conventional calorimetric analysis requires oxygen, and poor oxygen may lead to an insufficient reaction.

DISCLOSURE OF INVENTION

With the foregoing in mind, it is an object of the present invention to provide a colorimetric method that can achieve a short-time analysis and reliable values obtained by the analysis.

A colorimetric method of the present invention includes transferring an electron from an analyte to a coloring reagent that produces color by reduction via a mediator by using an oxidoreductase; and performing qualitative or quantitative analysis of the analyte by measuring color produced in the coloring reagent. The mediator is at least one selected from the group consisting of an iron complex, a ruthenium complex, an osmium complex, and a copper complex.

This method has only one enzyme reaction. Therefore, the reaction system is simple and has good stability. Moreover, the time between the enzyme reaction and the color production reaction is very short because the enzyme reaction system is simple and the mediator is used to reduce the coloring reagent. This also results in a shorter measuring time. For example, when glucose is used as a substrate in the colorimetric method of the present invention, the measurement can be performed in a short time (about 5 seconds or less). Further, a rapid reaction until color production can save the enzyme, so that the colorimetric method is advantageous in cost. This method allows the coloring reagent to produce color without relaying on hydrogen peroxide and requires no oxygen, thus ensuring highly reliable values obtained by the analysis.

A reagent of the present invention is used for the above calorimetric method. The reagent includes an oxidoreductase, a mediator, and a coloring reagent for producing color by reduction. A test piece of the present invention includes this reagent. Compared with a conventional test piece for colorimetric analysis that generates hydrogen peroxide, the test piece of the present invention can achieve a very short-time analysis and highly reliable values with the analysis.

BEST MODE FOR CARRYING OUT THE INVENTION

Figure 1:
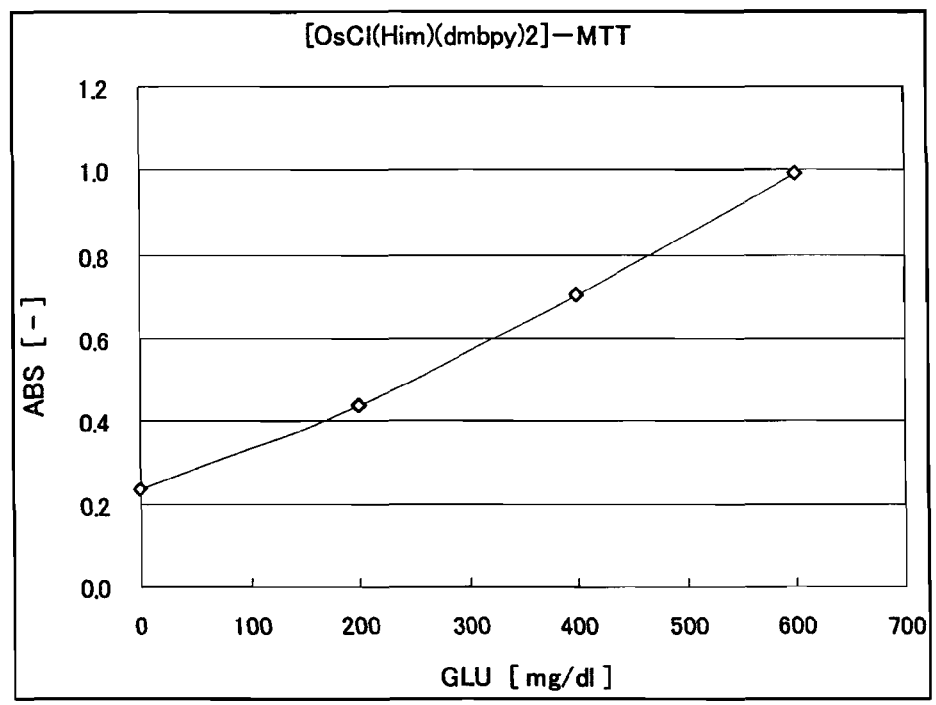
FIG. 1 is a graph showing the relationship between a glucose concentration and color production of an example of the present invention.

In a colorimetric method, a reagent, and a test piece of the present invention, the mediator is preferably an iron complex, a ruthenium complex, an osmium complex, a copper complex, or a mixture containing at least two of these complexes. It is preferable that a coordinating atom of a ligand in the complex is at least one selected from the group consisting of nitrogen, oxygen, and sulfur. It is preferable that the ligand is at least one selected from the group consisting of ammonia, a bipyridyl compound, an imidazole compound, a phenanthroline compound, an ethylenediamine compound, amino acid, a triazine compound, a biquinoline compound, a pyridylazo compound, a nitroso compound, an oxine compound, a benzothiazole compound, an acetylacetone compound, an anthraquinone compound, a xanthene compound, oxalic acid, and a derivative of each of the compounds. The complex may have two or more types of ligands, i.e., it can be a mixed ligand complex. At least one hydrogen atom that occupies a position other than the coordination position of the ligand may be replaced by a substituent. Examples of the substituent include an alkyl group, an aryl group, an allyl group, a phenyl group, a hydroxyl group, an alkoxy group, a carboxy group, a carbonyl group, a sulfone group, a sulfonyl group, a nitro group, a nitroso group, a primary amine, a secondary amine, a tertiary amine, an amino group, an acyl group, an amido group, and a halogen group.

In a colorimetric method, a reagent, and a test piece of the present invention, the oxidoreductase is preferably a dehydrogenase or an oxidase. The analyte is preferably, e.g., glucose, cholesterol, lactic acid, uric acid, pyruvic acid, creatine, or creatinine. In this case, a dehydrogenase or an oxidase that corresponds to each of the analytes is suitable for the oxidoreductase. A reaction rate increases with the quantity of enzyme. The coloring reagent is preferably a tetrazolium salt. It is preferable that the tetrazolium salt has at least one group selected from a nitrophenyl group, a thiazolyl group, and a benzothiazolyl group. Specifically, examples of the tetrazolium salt include MTT, INT, Neo-TB, Nitro-TB, TB, WST-1, WST-3, WST-4, WST-5, WST-8, 2-(2-benzothiazolyl)-3,5-diphenyltetrazolium bromide, 2-(2-benzothiazolyl)-3-(4-nitrophenyl)-5-phenyltetrazolium bromide, 2,3-bis(4-nitrophenyl)-5-phenyltetrazolium chloride, 2,3-di(4-nitrophenyl)tetrazolium perchlorate, 3-(3-nitrophenyl)-5-methyl-2-phenyltetrazolium chloride, and 3-(4-nitrophenyl)-5-methyl-2-phenyltetrazolium chloride.

A test piece of the present invention preferably includes an inorganic gel as well as the reagent. The inorganic gel serves to block oxygen, thereby preventing oxidation of a coloring reagent and fading of color produced in the coloring reagent due to reoxidation.

As described above, an iron complex, a ruthenium complex, an osmium complex, or a copper complex is suitable for the mediator of the present invention, and the osmium complex is particularly suitable.

Iron Complex

Examples of a ligand in the iron complex include ammonia, a bipyridyl compound, an imidazole compound, a phenanthroline compound, an ethylenediamine compound, amino acid, a triazine compound, a biquinoline compound, a pyridylazo compound, a nitroso compound, an oxine compound, a benzothiazole compound, an acetylacetone compound, an anthraquinone compound, a xanthene compound, oxalic acid, and a derivative of each of the compounds. A mixed ligand with two or more types of these ligands may be used.

For the bipyridyl compound, the coordination number is 6. The bipyridyl compound may be unsubstituted or substituted. The introduction of a substituent makes it possible to control, e.g., solubility and oxidation-reduction potential of the complex. Examples of the position of the substituent include the 4,4'-position and 5,5'-position. Examples of the substituent include an alkyl group (such as a methyl group, an ethyl group, or a propyl group), an aryl group, an allyl group, a phenyl group, a hydroxyl group, an alkoxy group (such as a methoxy group or an ethoxy group), a carboxy group, a carbonyl group, a sulfone group, a sulfonyl group, a nitro group, a nitroso group, a primary amine, a secondary amine, a tertiary amine, an amino group, an acyl group, an amido group, and a halogen group (such as bromine, chlorine, or iodine).

Examples of a bipyridyl iron complex include [Fe(bipyridyl)$_3$], [Fe(4,4'-dimethyl-2,2'-bipyridyl)$_3$], [Fe(4,4'-diphenyl-2,2'-bipyridyl)$_3$], [Fe(4,4'-diamino-2,2'-bipyridyl)$_3$], [Fe(4,4'-dihydroxy-2,2'-bipyridyl)$_3$], [Fe(4,4'-dicarboxy-2,2'-bipyridyl)$_3$], [Fe(4,4'-dibromo-2,2'-bipyridyl)$_3$], [Fe(5,5'-dimethyl-2,2'-bipyridyl)$_3$], [Fe(5,5'-diphenyl-2,2'-bipyridyl)$_3$], [Fe(5,5'-diamino-2,2'-bipyridyl)$_3$], [Fe(5,5'-dihydroxy-2,2'-bipyridyl)$_3$], [Fe(5,5'-dicarboxy-2,2'-bipyridyl)$_3$], and [Fe(5,5'-dibromo-2,2'-bipyridyl)$_3$].

For the imidazole compound, the coordination number is 6. The imidazole compound may be unsubstituted or substituted. The introduction of a substituent makes it possible to control, e.g., solubility and oxidation-reduction potential of the complex. Examples of the position of the substituent include the 2-position, 4-position and 5-position. Examples of the substituent include an alkyl group (such as a methyl group, an ethyl group, or a propyl group), an aryl group, an allyl group, a phenyl group, a hydroxyl group, an alkoxy group (such as a methoxy group or an ethoxy group), a carboxy group, a carbonyl group, a sulfone group, a sulfonyl group, a nitro group, a nitroso group, a primary amine, a secondary amine, a tertiary amine, an amino group, an acyl group, an amido group, and a halogen group (such as bromine, chlorine, or iodine).

Examples of an imidazole iron complex include [Fe(imidazole)$_6$], [Fe(4-methyl-imidazole)$_6$], [Fe(4-phenyl-imidazole)$_6$], [Fe(4-amino-imidazole)$_6$], [Fe(4-hydroxy-imidazole)$_6$], [Fe(4-carboxy-imidazole)$_6$], and [Fe(4-bromo-imidazole)$_6$].

The amino acid includes, e.g., arginine (L-Arg). An arginine iron complex generally has the advantage of high solubility. The mixed ligand may be a combination of the bipyridyl compounds and the imidazole compounds or a combination of the bipyridyl compounds and amino acid, such as [Fe(imidazole)$_2$(bipyridyl)$_2$] or [Fe(L-Arg)$_2$(bipyridyl)$_2$]. The use of the mixed ligand can impart various properties to the complex, e.g., arginine improves the solubility of the complex.

Ruthenium Complex

Examples of a ligand in the ruthenium complex include ammonia, a bipyridyl compound, an imidazole compound, a phenanthroline compound, an ethylenediamine compound, amino acid, a triazine compound, a biquinoline compound, a pyridylazo compound, a nitroso compound, an oxine compound, a benzothiazole compound, an acetylacetone compound, an anthraquinone compound, a xanthene compound, oxalic acid, and a derivative of each of the compounds. A mixed ligand with two or more types of these ligands may be used.

For the bipyridyl compound, the coordination number is 6. The bipyridyl compound may be unsubstituted or substituted. The introduction of a substituent makes it possible to control, e.g., solubility and oxidation-reduction potential of the complex. Examples of the position of the substituent include the 4,4'-position and 5,5'-position. Examples of the substituent include an alkyl group (such as a methyl group, an ethyl group, or a propyl group), an aryl group, an allyl group, a phenyl group, a hydroxyl group, an alkoxy group (such as a methoxy group or an ethoxy group), a carboxy group, a carbonyl group, a sulfone group, a sulfonyl group, a nitro group, a nitroso group, a primary amine, a secondary amine, a tertiary amine, an amino group, an acyl group, an amido group, and a halogen group (such as bromine, chlorine, or iodine).

Examples of a bipyridyl ruthenium complex include [Ru(bipyridyl)$_3$], [Ru(4,4'-dimethyl-2,2'-bipyridyl)$_3$], [Ru(4,4'- diphenyl-2,2'-bipyridyl)$_3$], [Ru(4,4'-diamino-2,2'-bipyridyl)$_3$], [Ru(4,4'-dihydroxy-2,2'-bipyridyl)$_3$], [Ru(4,4'-dicarboxy-2,2'-bipyridyl)$_3$], [Ru(4,4'-dibromo-2,2'-bipyridyl)$_3$], [Ru(5,5'-dimethyl-2,2'-bipyridyl)$_3$], [Ru(5,5'-diphenyl-2,2'-bipyridyl)$_3$], [Ru(5,5'-diamino-2,2'-bipyridyl)$_3$], [Ru(5,5'-dihydroxy-2,2'-bipyridyl)$_3$], [Ru(5,5'-dicarboxy-2,2'-bipyridyl)$_3$], and [Ru(5,5'-dibromo-2,2'-bipyridyl)$_3$].

For the imidazole compound, the coordination number is 6. The imidazole compound may be unsubstituted or substituted. The introduction of a substituent makes it possible to control, e.g., solubility and oxidation-reduction potential of the complex. Examples of the position of the substituent include the 2-position, 4-position and 5-position. Examples of the substituent include an alkyl group (such as a methyl group, an ethyl group, or a propyl group), an aryl group, an allyl group, a phenyl group, a hydroxyl group, an alkoxy group (such as a methoxy group or an ethoxy group), a carboxy group, a carbonyl group, a sulfone group, a sulfonyl group, a nitro group, a nitroso group, a primary amine, a secondary amine, a tertiary amine, an amino group, an acyl group, an amido group, and a halogen group (such as bromine, chlorine, or iodine).

Examples of an imidazole ruthenium complex include [Ru(imidazole)$_6$], [Ru(4-methyl-imidazole)$_6$], [Ru(4-phenyl-imidazole)$_6$][Ru(4-amino-imidazole)$_6$], [Ru(4-hydroxy-imidazole)$_6$], [Ru(4-carboxy-imidazole)$_6$], and [Ru(4-bromo-imidazole)$_6$].

The amino acid includes, e.g., arginine (L-Arg). An arginine ruthenium complex generally has the advantage of high solubility. The mixed ligand may be a combination of the bipyridyl compounds and the imidazole compounds or a combination of the bipyridyl compounds and amino acid, such as [Ru(imidazole)$_2$(bipyridyl)$_2$] or [Ru(L-Arg)$_2$(bipyridyl)$_2$]. The use of the mixed ligand can impart various properties to the complex, e.g., arginine improves the solubility of the complex.

Osmium Complex

Examples of a ligand in the osmium complex include ammonia, a bipyridyl compound, an imidazole compound, a phenanthroline compound, an ethylenediamine compound, amino acid, a triazine compound, a biquinoline compound, a pyridylazo compound, a nitroso compound, an oxine compound, a benzothiazole compound, an acetylacetone compound, an anthraquinone compound, a xanthene compound, oxalic acid, and a derivative of each of the compounds. A mixed ligand with two or more types of these ligands may be used.

For the bipyridyl compound, the coordination number is 6. The bipyridyl compound may be unsubstituted or substituted. The introduction of a substituent makes it possible to control, e.g., solubility and oxidation-reduction potential of the complex. Examples of the position of the substituent include the 4,4'-position and 5,5'-position. Examples of the substituent include an alkyl group (such as a methyl group, an ethyl group, or a propyl group), an aryl group, an allyl group, a phenyl group, a hydroxyl group, an alkoxy group (such as a methoxy group or an ethoxy group), a carboxy group, a carbonyl group, a sulfone group, a sulfonyl group, a nitro group, a nitroso group, a primary amine, a secondary amine, a tertiary amine, an amino group, an acyl group, an amido group, and a halogen group (such as bromine, chlorine, or iodine).

Examples of a bipyridyl osmium complex include [Os(bipyridyl)$_3$], [Os(4,4'-dimethyl-2,2'-bipyridyl)$_3$], [Os(4,4'-diphenyl-2,2'-bipyridyl)$_3$], [Os(4,4'-diamino-2,2'-bipyridyl)$_3$], [Os(4,4'-dihydroxy-2,2'-bipyridyl)$_3$], [Os(4,4'-dicarboxy-2,2'-bipyridyl)$_3$], [Os(4,4'-dibromo-2,2'-bipyridyl)$_3$], [Os(5,5'-dimethyl-2,2'-bipyridyl)$_3$], [Os(5,5'-diphenyl-2,2'-bipyridyl)$_3$], [Os(5,5'-diamino-2,2'-bipyridyl)$_3$], [Os(5,5'-dihydroxy-2,2'-bipyridyl)$_3$], [Os(5,5'-dicarboxy-2,2'-bipyridyl)$_3$], and [Os(5,5'-dibromo-2,2'-bipyridyl)$_3$].

For the imidazole compound, the coordination number is 6. The imidazole compound may be unsubstituted or substituted. The introduction of a substituent makes it possible to control, e.g., solubility and oxidation-reduction potential of the complex. Examples of the position of the substituent include the 2-position, 4-position and 5-position. Examples of the substituent include an alkyl group (such as a methyl group, an ethyl group, or a propyl group), an aryl group, an allyl group, a phenyl group, a hydroxyl group, an alkoxy group (such as a methoxy group or an ethoxy group), a carboxy group, a carbonyl group, a sulfone group, a sulfonyl group, a nitro group, a nitroso group, a primary amine, a secondary amine, a tertiary amine, an amino group, an acyl group, an amido group, and a halogen group (such as bromine, chlorine, or iodine).

Examples of an imidazole osmium complex include [Os(imidazole)$_6$], [Os(4-methyl-imidazole)$_6$], [Os(4-phenyl-imidazole)$_6$], [Os(4-amino-imidazole)$_6$], [Os(4-hydroxy-imidazole)$_6$], [Os(4-carboxy-imidazole)$_6$], and [Os(4-bromo-imidazole)$_6$].

The amino acid includes, e.g., arginine (L-Arg). An arginine osmium complex generally has the advantage of high solubility. The mixed ligand may be a combination of the bipyridyl compounds and the imidazole compounds or a combination of the bipyridyl compounds and amino acid, such as [Os(imidazole)$_2$(bipyridyl)$_2$] or [Os(L-Arg)$_2$(bipyridyl)$_2$]. The use of the mixed ligand can impart various properties to the complex, e.g., arginine improves the solubility of the complex.

Copper Complex

Examples of a ligand in the copper complex include ammonia, a bipyridyl compound, an imidazole compound, a phenanthroline compound, an ethylenediamine compound, amino acid, a triazine compound, a biquinoline compound, a pyridylazo compound, a nitroso compound, an oxine compound, a benzothiazole compound, an acetylacetone compound, an anthraquinone compound, a xanthene compound, oxalic acid, and a derivative of each of the compounds. A mixed ligand with two or more types of these ligands may be used.

For the bipyridyl compound, the coordination number is 4 or 6. In view of stability, the bipyridyl compound should be coordinated at two positions in the complex. The bipyridyl compound may be unsubstituted or substituted. The introduction of a substituent makes it possible to control, e.g., solubility and oxidation-reduction potential of the complex. Examples of the position of the substituent include the 4,4'-position and 5,5'-position. Examples of the substituent include an alkyl group (such as a methyl group, an ethyl group, or a propyl group), an aryl group, an allyl group, a phenyl group, a hydroxyl group, an alkoxy group (such as a methoxy group or an ethoxy group), a carboxy group, a carbonyl group, a sulfone group, a sulfonyl group, a nitro group, a nitroso group, a primary amine, a secondary amine, a tertiary amine, an amino group, an acyl group, an amido group, and a halogen group (such as bromine, chlorine, or iodine).

Examples of a bipyridyl copper complex include [Cu(bipyridyl)$_2$], [Cu(4,4'-dimethyl-2,2'-bipyridyl)$_2$], [Cu(4,4'-diphenyl-2,2'-bipyridyl)$_2$], [Cu(4,4'-diamino-2,2'-bipyridyl)$_2$], [Cu(4,4'-dihydroxy-2,2'-bipyridyl)$_2$], [Cu(4,4'-dicarboxy-2,2'-bipyridyl)$_2$], [Cu(4,4'-dibromo-2,2'-bipyridyl)$_2$], [Cu(5,5'-dimethyl-2,2'-bipyridyl)$_2$], [Cu(5,5'-diphenyl-2,2'-bipyridyl)$_2$], [Cu(5,5'-diamino-2,2'-bipyridyl)$_2$], [Cu(5,5'-dihydroxy-2,2'-bipyridyl)$_2$], [Cu(5,5'-dicarboxy-2, 2'-bipyridyl)$_2$], [Cu(5,5'-dibromo-2,2'-bipyridyl)$_2$], [Cu(bipyridyl)$_3$], [Cu(4,4'-dimethyl-2,2'-bipyridyl)$_3$], [Cu(4,4'-diphenyl-2,2'-bipyridyl)$_3$], [Cu(4,4'-diamino-2,2'-bipyridyl)$_3$], [Cu(4,4'-dihydroxy-2,2'-bipyridyl)$_3$], [Cu(4,4-dicarboxy-2,2'-bipyridyl)$_3$], [Cu(4,4'-dibromo-2,2'-bipyridyl)$_3$], [Cu(5,5'-dimethyl-2,2'-bipyridyl)$_3$], [Cu(5,5'-diphenyl-2,2'-bipyridyl)$_2$], [Cu(5,5'-diamino-2,2'-bipyridyl)$_3$], [Cu(5,5'-dihydroxy-2,2'-bipyridyl)$_3$], [Cu(5,5'-dicarboxy-2,2'-bipyridyl)$_3$], and [Cu(5,5'-dibromo-2,2'-bipyridyl)$_3$].

For the imidazole compound, the coordination number is 4. The imidazole compound may be unsubstituted or substituted. The introduction of a substituent makes it possible to control, e.g., solubility and oxidation-reduction potential of the complex. Examples of the position of the substituent include the 2-position, 4-position and 5-position. Examples of the substituent include an alkyl group (such as a methyl group, an ethyl group, or a propyl group), an aryl group, an allyl group, a phenyl group, a hydroxyl group, an alkoxy group (such as a methoxy group or an ethoxy group), a carboxy group, a carbonyl group, a sulfone group, a sulfonyl group, a nitro group, a nitroso group, a primary amine, a secondary amine, a tertiary amine, an amino group, an acyl group, an amido group, and a halogen group (such as bromine, chlorine, or iodine).

Examples of an imidazole copper complex include [Cu(imidazole)$_4$], [Cu(4-methyl-imidazole)$_4$], [Cu(4-phenyl-imidazole)$_4$], [Cu(4-amino-imidazole)$_4$], [Cu(4-hydroxy-imidazole)$_4$], [Cu(4-carboxy-imidazole)$_4$], and [Cu(4-bromo-imidazole)$_4$].

The amino acid includes, e.g., arginine (L-Arg). An arginine copper complex generally has the advantage of high solubility. The mixed ligand may be a combination of the bipyridyl compounds and the imidazole compounds or a combination of the bipyridyl compounds and amino acid, such as [Cu(imidazole)$_2$(bipyridyl)] or [Cu(L-Arg)$_2$(bipyridyl)]. The use of the mixed ligand can impart various properties to the complex, e.g., arginine improves the solubility of the complex.

The above explanation of the transition metal complexes is based on the type of transition metal, and the present invention is not limited thereto. Hereinafter, the transition metal complexes will be described based on their ligands.

A ligand contains coordinating atoms N, O, and S has groups such as =N—OH, —COOH, —OH, —SH, >C=O in the molecule. Examples of metal complexes including this type of ligand are NN chelate, NO chelate, NS chelate, OO chelate, OS chelate, SS chelate (bidentate), N chelate (unidentate), and NNN chelate (tridentate). The combination is diverse. When a ligand has a double bond, Cu, Fe, Ru, and Os of the complex tend to have the function of transferring/receiving electrons. The ligand preferably has an aromatic ring. As described above, various substituents may be introduced into the ligand. For example, the introduction of a sulfone group can improve the solubility of the metal complex. The metal complex may be formed by mixing two or more types of ligands and used as a mixed ligand complex. For example, when one of the ligands is amino acid, the metal complex may have a good affinity with an enzyme. Moreover, various halogen atoms (such as Cl, F, Br, and I) can be attached to part of the site of the central metal. The following is an example of the transfer metal complexes that are classified by the type of coordination.

N,N-Coordination Form
Phenanthroline derivative
Cu+1,10-phenanthroroline
Fe+1,10-phenanthroroline
Cu+bathophenanthroline
Fe+bathophenanthroline
Cu+bathophenanthroline sulfonic acid
Fe+bathophenanthroline sulfonic acid
Bipyridyl derivative
Cu+2,2'-bipyridyl
Fe+2,2'-bipyridyl
Fe+4,4'-diamino-2,2'-bipyridyl
Ru+4,4'-diamino-2,2'-bipyridyl
Triazine derivative
Cu+TPTZ (2,4,6-tripyridyl-S-triazine)
Fe+TPTZ (2,4,6-tripyridyl-S-triazine)
Fe+PDTS (3-(2-pyridyl)-5,6-bis(4-sulfophenyl)-1,2,4-triazine)
Biquinoline derivative
Cu+cuproin (2,2'-biquinoline)
Pyridylazo derivative
Fe+nitro-PAPS (2-(5-nitro-2-pyridylazo)-5-[N-n-propyl-N-(3-sulfopropyl)amino]phenol)
NO Coordination Form
Fe+nitroso-PSAP (2-nitroso-5-[N-n-propyl-N-(3-sulfopropyl)amino]phenol)
Fe+nitroso-ESAP (2-nitroso-5-[N-ethyl-N-(3-sulfopropyl)amino]phenol)
Fe+1-nitroso-2-naphthol
NS Coordination Form
Fe+2-amino-4-thiazole acetic acid
OO Coordination Form
Fe+1,2-naphthoquinone-4-sulfonic acid
Mixed Ligand Form
Os+Cl, imidazole, 4,4'-dimethyl-2,2'-bipyridyl
Os+imidazole, 4,4'-dimethyl-2,2'-bipyridyl
Cu+L-arginine, 2,2'-bipyridyl
Cu+ethylenediamine, 2,2'-bipyridyl
Cu+imidazole, 2,2'-bipyridyl The coloring reagent of the present invention is not particularly limited and can be
2-(4-iodophenyl)-3-(4-nitorophenyl)-5-phenyl-2H-tetrazolium chloride (INT),
3-(4,5-dimethyl-2-thiazolyl)-2,5-diphenyl-2H-tetrazolium bromide (MTT),
3,3'-(1,1'-biphenyl-4,4'-diyl)-bis(2,5-diphenyl-2H-tetrazolium chloride) (Neo-TB),
3,3'-[3,3'-dimethoxy-(1,1'-biphenyl)-4,4'-diyl]-bis[2-(4-nitrophenyl)-5-phenyl-2 H-tetrazolium chloride (Nitro-TB),
3,3'-[3,3'-dimethoxy-(1,1'-biphenyl)-4,4'-diyl]-bis(2,5-diphenyl-2H-tetrazolium chloride) (TB),
2-(4-iodophenyl)-3-(4-nitrophenyl)-5-(2,4-disulfophenyl)-2H-tetrazolium, monosodium salt (WST-1),
2-(4-iodophenyl)-3-(2,4-dinitrophenyl)-5-(2,4-disulfophenyl)-2H-tetrazolium, monosodium salt (WST-3),
2-benzothiazolyl-3-(4-carboxy-2-methoxyphenyl)-5-[4-(2-sulfoethylcarbamoyl)phenyl]-2H-tetrazolium (WST-4),
2,2'-dibenzothiazolyl-5,5'-bis[4-di(2-sulfoethyl)carbamoylphenyl]-3,3'-(3,3'-dimethoxy-4,4'-biphenylene)ditetrazolium, disodium salt (WST-5),
2-(2-methoxy-4-nitrophenyl)-3-(4-nitrophenyl)-5-(2,4-disulfophenyl)-2H-tetrazolium, monosodium salt (WST-8),
2-(2-benzothiazolyl)-3,5-diphenyltetrazolium bromide,
2-(2-benzothiazolyl)-3-(4-nitrophenyl)-5-phenyltetrazolium bromide,
2,3-bis(4-nitrophenyl)-5-phenyltetrazolium chloride,
2,3-di(4-nitrophenyl)tetrazolium perchlorate,
3-(3-nitrophenyl)-5-methyl-2-phenyltetrazolium chloride,
3-(4-nitrophenyl)-5-methyl-2-phenyltetrazolium chloride, an iron complex, or a copper complex. The iron complex and the copper complex, which function as a mediator, also can be used as a coloring reagent in the present invention.

As described above, examples of the copper complex include a bipyridyl copper complex, an imidazole copper complex, an amino acid (e.g., arginine) copper complex, an imidazole-bipyridyl copper complex, and an imidazole-amino acid copper complex. The color of the copper complex is changed from blue ($Cu^{2+}$) to reddish brown ($Cu^+$) by electron transfer. When the copper complex is used as a coloring reagent, any transition metal complex other than copper complex can be used as the mediator, and an osmium complex and a ruthenium complex are preferred.

Next, a calorimetric method of the present invention is applied to a test piece. In this case, an osmium complex is used as the mediator, MTT is used as the coloring reagent, and glucose is used as the analyte. Other analytes, such as cholesterol, are analyzed basically in the same manner except that the oxidoreductase is changed according to each of the analytes.

First, an osmium complex is prepared. The osmium complex can be a commercially available product. Alternatively, it can be produced by any method described in the following examples. The osmium complex is dissolved in a buffer solution, and then MTT, additives (e.g., a binder), and glucose dehydrogenase (GDH) are dissolved in the solution, resulting in a reagent solution. The buffer solution can be a phosphate buffer, Good's buffer, or the like. The concentration of the osmium complex with respect to the total buffer solution ranges, e.g., from 1 to 10 wt %. Examples of the binder include hydroxypropylcellulose (HPC), polyvinyl alcohol (PVA), polyvinyl pyrrolidone (PVP), polyacrylamide, and bovine serum albumin (BSA), and HPC is preferred. The concentration of the binder ranges, e.g., from 0.5 to 5 wt %. The concentration of GDH ranges, e.g., from 1000 to 50000 U/ml. The concentration of MTT is not particularly limited. A porous sheet (e.g., a filter paper) is impregnated with the reagent solution and dried, thereby producing a test piece for glucose analysis. Before impregnation of the reagent solution, it is preferable that the porous sheet is impregnated with an inorganic gel solution and dried. The inorganic gel can be smectite or the like. The concentration of the inorganic gel in the solution ranges, e.g., from 1 to 5 wt %, preferably 1 to 3 wt %, and more preferably 1.5 to 2 wt %. The inorganic gel solution also may include an amphoteric surfactant such as CHAPS. The concentration of the amphoteric surfactant with respect to the total inorganic gel solution ranges, e.g., from 0.1 to 2 wt %, preferably 0.1 to 1 wt %, and more preferably 0.2 to 0.4 wt %. The amount of inorganic gel impregnated into the porous sheet ranges, e.g., from 1 to 50 mg/cm$^3$, preferably 10 to 30 mg/cm$^3$, and more preferably 15 to 20 mg/cm$^3$, when measured on the basis of the volume of voids in the porous sheet. The porous sheet can be an asymmetrical porous film, in which a pore size varies in the thickness direction or in the sheet surface direction. When a sample containing glucose (e.g., blood) is dropped on the test piece, MTT produces color in accordance with the glucose concentration. Therefore, the qualitative or quantitative analysis can be performed by measuring the degree of color production. The time required for the analysis is about 1 to 3 seconds after dropping the sample. If the test piece is impregnated with an inorganic gel, the color can be more uniform and stable.

The inorganic gel is preferably swelling clay minerals. Among the swelling clay minerals, bentonite, smectite, vermiculite, or synthetic fluorine mica is more preferred. In particular, synthetic smectite such as synthetic hectorite or synthetic saponite, or synthetic mica (the natural mica generally is a non-swelling clay mineral) such as swelling synthetic mica (or Na mica) typified by synthetic fluorine mica is preferred.

Next, a colorimetric method of the present invention is applied to liquid system analysis. In this case, an osmium complex is used as the mediator, MTT is used as the coloring reagent, and glucose is used as the analyte. Other analytes, such as cholesterol, are analyzed basically in the same manner except that the oxidoreductase is changed according to each of the analytes.

A reagent solution is prepared by dissolving the osmium complex, GDH, and MTT in a buffer solution. Although these may be dissolved in water, the buffer solution is preferred. The pH of the buffer solution ranges, e.g., from 6 to 8, and preferably 6.5 to 7. The concentration of the osmium complex ranges, e.g., from 0.1 to 60 mM, preferably 0.2 to 10 mM, and more preferably 0.3 to 0.6 mM. The concentration of GDH ranges, e.g., from 10 to 1000 U/ml, preferably 50 to 500 U/ml, and more preferably 100 to 200 U/ml. The concentration of MTT is not particularly limited. When a sample containing glucose (e.g., blood) is added to the reagent solution, the reagent solution produces color in accordance with the glucose concentration in a short time, e.g., 5 seconds or less. This change may be observed visually or measured with an optical measuring device such as a spectrophotometer. The amount of the added sample ranges, e.g., from 1 to 100 μl, preferably 3 to 10 μl, and more preferably 5 to 10 μl with respect to 1 ml of the reagent solution.

EXAMPLES

Hereinafter, examples of the present invention will be described. In each of the examples, PQQ represents pyrroloquinoline quinone, and other reagents are explained in detail in the following table.

| Reagent | Manufacturer | Note (name, etc.) |
| --- | --- | --- |
| PQQGDH | TOYOBO Co., Ltd | PQQ-Glucose Dehyrogenase |
| GOD | Sigma | Glucose Oxidase Type X-S |
| Pyruvate Oxidase | BoehringerMannheim | |
| MTT | DOJINDO LABORATORIES | 3-(4,5-dimethyl-2-thiazolyl)-2,5-diphenyl-2H-tetrazolium bromide |
| WST-4 | DOJINDO LABORATORIES | 2-benzothiazolyl-3-(4-carboxy-2-methoxyphenyl)-5-[4-(2-sulfoethylcarbamoyl)phenyl]-2H-tetrazolium |
| WST-5 | DOJINDO LABORATORIES | 2,2'-dibenzothiazolyl-5,5'-bis[4-di(2-sulfoethyl)carbamoylphenyl]-3,3'-(3,3'-dimethoxy-4,4'-biphenylene) ditetrazolium, disodium salt |
| Glucose | Wako Pure Chemical Industries, Ltd. | D(+)-Glucose |
| Pyruvic acid | Wako Pure Chemical Industries, Ltd. | Lithium Pyruvate Monohydrate |

Example 1

An osmium complex [OsCl(Him)(dmbpy)$_2$] was synthesized. First, 2.00 g (4.56 mmol) of (NH$_4$)$_2$[OsCl$_6$] and 1.68 g (9.11 mmol) of dimethylbipyridyl (dmbpy) were refluxed in ethylene glycol (60 ml) for 1 hour under a nitrogen stream. After cooling to room temperature, 1M sodium hydrosulfite solution (120 ml) was added for 30 minutes, followed by cooling in an ice bath for 30 minutes. The precipitates thus produced were filtered under reduced pressure and sufficiently washed with water (500 to 1000 ml). Further, the precipitates were washed two times with diethyl ether, and then dried under reduced pressure. Thus, 1.5 to 1.7 g of [OsCl$_2$(dmbpy)$_2$] was obtained. Next, 1.56 g (2.60 mmol) of the resultant [OsCl$_2$(dmbpy)$_2$] and 0.36 g (5.2 mmol) of imidazole (Him) were refluxed in a water/methanol mixed solvent (50 ml) for 2 hours under a nitrogen stream. After cooling to room temperature, a saturated NaCl solution (300 ml) was added. The precipitates thus produced were filtered under reduced pressure, washed with a saturated NaCl solution, and dried under reduced pressure. Thus, [OsCl(Him)(dmbpy)$_2$]Cl$_2$ was obtained. The [OsCl(Him)(dmbpy)$_2$]Cl$_2$ was dissolved in the smallest possible amount of acetonitrile/methanol (1:1 v/v) and purified by column chromatography (an absorbent: activated alumina, a developing solvent: acetonitrile/methanol). The solvent was evaporated, the residue was dissolved in a small amount of acetone, and reprecipitated with diethyl ether. The precipitates thus produced were filtered and dried under reduced pressure, resulting in purified [OsCl(Him)(dmbpy)$_2$]Cl$_2$.

The following reagent solution including the osmium complex was prepared. First, 5 μl of glucose (GLU) solution with different concentrations (0, 200, 400, 600 mg/100 ml) was placed in a microcell (made of polymethacrylate) having an optical path length of 10 mm. Then, 1000 μl of the reagent solution was added, and the absorbance was immediately measured at a wavelength of 600 nm. FIG. 1 shows the results. The graph indicates that the color was produced in accordance with the glucose concentration. Since the reaction was performed rapidly, it took substantially only 2 seconds before the substrate was consumed completely.

Reagent Solution Composition

| MTT (DOJINDO LABORATORIES) | 0.5 mM |
| [OsCl(Him)(dmbpy)$_2$]Cl$_2$ | 0.1 mM |
| PIPES (pH 7.0) | 40 mM |
| PQQGDH | 200 U/ml |

Example 2

Figure 2:
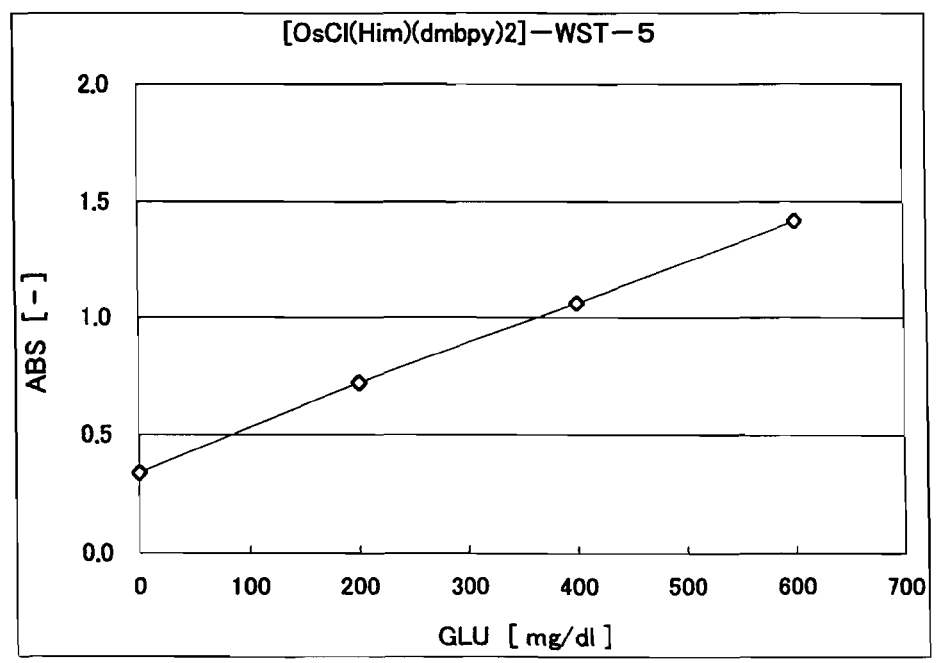
FIG. 2 is a graph showing the relationship between a glucose concentration and color production of another example of the present invention.

The following reagent solution including the osmium complex was prepared. First, 5 μl of glucose (GLU) solution with different concentrations (0, 200, 400, 600 mg/100 ml) was placed in a microcell (made of polymethacrylate) having an optical path length of 10 mm. Then, 1000 μl of the reagent solution was added, and the absorbance was immediately measured at a wavelength of 600 nm. FIG. 2 shows the results. The graph indicates that the color was produced in accordance with the glucose concentration. Since the reaction was performed rapidly, it took substantially only 1 second before the substrate was consumed completely.

Reagent Solution Composition

| WST-5 (DOJINDO LABORATORIES) | 0.5 mM |
| [OsCl(Him)(dmbpy)$_2$]Cl$_2$ | 0.1 mM |
| PIPES (pH 7.0) | 40 mM |
| PQQGDH | 200 U/ml |

Example 3

Figure 3:
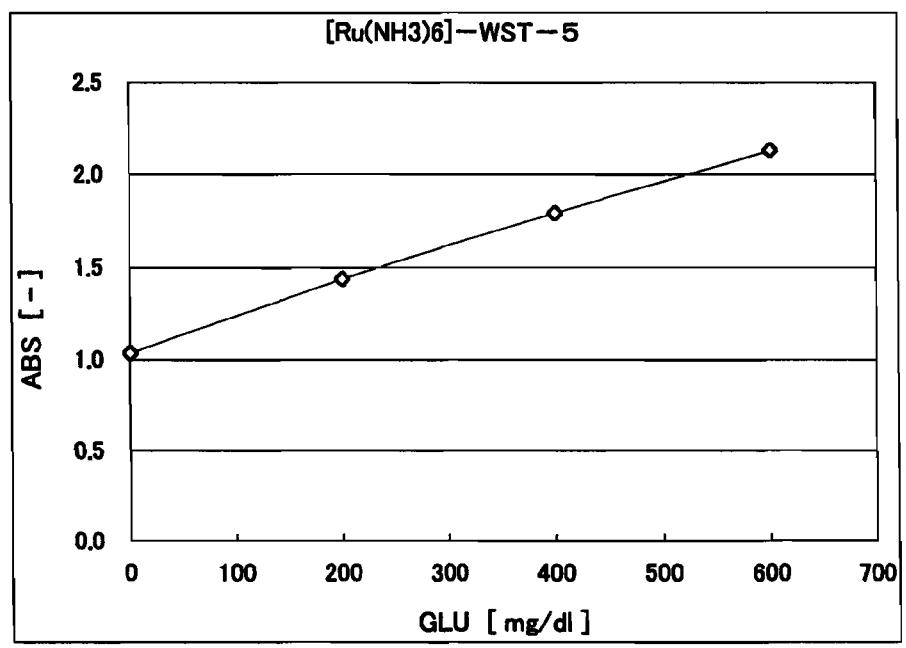
FIG. 3 is a graph showing the relationship between a glucose concentration and color production of yet another example of the present invention.

The following reagent solution including a ruthenium complex was prepared. First, 5 μl of glucose (GLU) solution with different concentrations (0, 200, 400, 600 mg/100 ml) was placed in a microcell (made of polymethacrylate) having an optical path length of 10 mm. Then, 1000 μl of the reagent solution was added, and the absorbance was immediately measured at a wavelength of 600 nm. FIG. 3 shows the results. The graph indicates that the color was produced in accordance with the glucose concentration. Since the reaction was performed rapidly, it took substantially only 2 seconds before the substrate was consumed completely.

Reagent Solution Composition

| WST-5 (DOJINDO LABORATORIES) | 0.5 mM |
| [Ru(NH$_3$)$_6$]Cl$_3$ (Aldrich) | 10 mM |
| PIPES (pH 7.0) | 40 mM |
| PQQGDH | 200 U/ml |

Example 4

Figure 4:
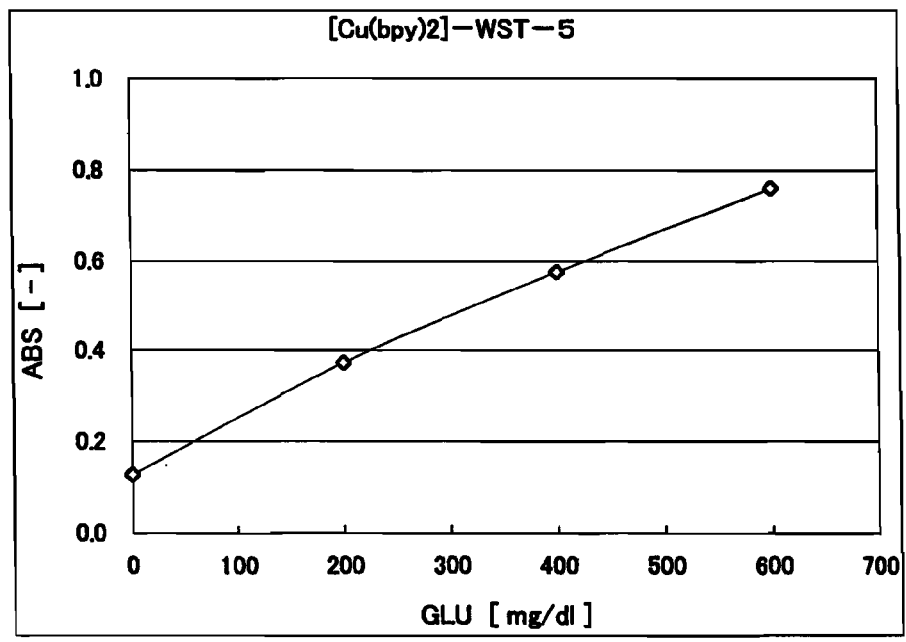
FIG. 4 is a graph showing the relationship between a glucose concentration and color production of still another example of the present invention.

CuCl$_2$ and 2,2'-bipyridyl (bpy) were mixed at a molar ratio of 1:2 in a water bath at about 80° C. and synthesized into [Cu(bpy)$_2$]Cl$_2$. The following reagent solution including this complex was prepared. First, 5 μl of glucose (GLU) solution with different concentrations (0, 200, 400, 600 mg/100 ml) was placed in a microcell (made of polymethacrylate) having an optical path length of 10 mm. Then, 1000 μl of the reagent solution was added, and the absorbance was immediately measured at a wavelength of 600 nm. FIG. 4 shows the results. The graph indicates that the color was produced in accordance with the glucose concentration. Since the reaction was performed rapidly, it took substantially only 2 seconds before the substrate was consumed completely.

Reagent Solution Composition

| WST-5 (DOJINDO LABORATORIES) | 0.5 mM |
| [Cu(bpy)$_2$]Cl$_2$ | 1 mM |
| PIPES (pH 7.0) | 40 mM |
| PQQGDH | 200 U/ml |

Example 5

A copper complex was prepared by using various ligands. Copper chloride (II) and each of the following ligands were mixed at a molar ratio of 1:2, dissolved in purified water, and incubated for 10 minutes in a water bath at about 80° C. so that the ligands were coordinated to the metal of the complex. Thus, a complex solution was obtained.

| Ligand | Manufacturer | Complex |
| --- | --- | --- |
| 1,10-phenanthroline | Wako Pure Chemical Industries, Ltd. | [Cu(1,10-phenanthroline)$_2$] |
| bathophenanthroline | Wako Pure Chemical Industries, Ltd. | [Cu(bathophenanthroline)$_2$] |
| bathophenanthroline sulfonic acid disodium salt | Nacalai Tesque, Inc. | [Cu(bathophenanthroline sulfonic acid)$_2$] |
| 2,2'-bipyridyl | Wako Pure Chemical Industries, Ltd. | [Cu(2,2'-bipyridyl)$_2$] |
| TPTZ | DOJINDO LABORATORIES | [Cu(TPTZ)$_2$] |
| cuproin | Wako Pure Chemical Industries, Ltd. | [Cu(cuproin)$_2$] |

Example 6

A copper mixed ligand complex was prepared by using each of the following ligands and the bipyridyl compounds. Copper, each of the following ligand, and the bipyridyl compounds were mixed at a molar ratio of 1:2:1, dissolved in purified water, and incubated for 10 minutes in a water bath at about 80° C. so that the ligands and the bipyridyl compounds were coordinated to the metal. Thus, a complex solution was obtained.

| Ligand | Manufacturer | Complex |
| --- | --- | --- |
| L-arginine | Nacalai Tesque, Inc. | [Cu(L-Arg)(bpy)] |
| ethylenediamine | Nacalai Tesque, Inc. | [Cu(en)(bpy)] |
| imidazole | Wako Pure Chemical Industries, Ltd. | [Cu(Him)(bpy)] |

Example 7

A copper complex was prepared by using various ligands. Iron chloride (III) and each of the following ligands were mixed at a molar ratio of 1:3, dissolved in purified water, and incubated for 10 minutes in a water bath at about 80° C. so that the ligands were coordinated to the metal. Thus, a complex solution was obtained.

| Ligand | Manufacturer | Complex |
| --- | --- | --- |
| 1,10-phenanthroline | Wako Pure Chemical Industries, Ltd. | [Fe(1,10-phenanthroline)$_3$] |
| bathophenanthroline | Wako Pure Chemical Industries, Ltd. | [Fe(bathophenanthroline)$_3$] |
| bathophenanthroline sulfonic acid disodium salt | Nacalai Tesque, Inc. | [Fe(bathophenanthroline sulfonic acid)$_3$] |
| 2,2'-bipyridyl | Wako Pure Chemical Industries, Ltd. | [Fe(2,2'-bipyridyl)$_3$] |
| 4,4'-diamino-2,2'-bipyridyl | Arkray, Inc. | [Fe(4,4'-diamino-2,2'-bipyridyl)$_3$] |
| TPTZ | DOJINDO LABORATORIES | [Fe(TPTZ)$_3$] |
| PDTS | DOJINDO LABORATORIES | [Fe(PDTS)$_3$] |
| nitro-PAPS | DOJINDO LABORATORIES | [Fe(nitroso-PAPS)$_3$] |
| nitroso-ESAP | DOJINDO LABORATORIES | [Fe(nitroso-ESAP)$_3$] |
| 1-nitroso-2-naphthol | KANTO KAGAKU | [Fe(1-nitroso-2-naphthol)$_3$] |
| 2-amino-4-thiazole acetic acid | Lancaster | [Fe(2-amino-4-thiazole acetic acid)$_3$] |
| 1,2-naphthoquinone-4-sulfonic acid | Nacalai Tesque, Inc. | [Fe(1,2-naphthoquinone-4-sulfonic acid)$_3$] |
| nitroso-PSAP | DOJINDO LABORATORIES | [Fe(nitroso-PSAP)$_3$] |

Example 8

Two types of ruthenium complexes were prepared in the following manner.

[Ru(NH$_3$)$_6$]

A commercially available ruthenium complex (manufactured by Aldrich, Hexammineruthenium(III) chloride) was dissolved in water to obtain a complex solution of [Ru(NH$_3$)$_6$].

[Ru(4,4'-diamino-2,2'-bipyridyl)$_3$]

Ligand

First, 11.8 g (63.0 mmol) of 2,2'-bipyridil-N,N'-dioxide (manufactured by Aldrich) was dissolved slowly in 120 ml of concentrated sulfuric acid cooled in an ice bath, and the resultant solution was heated to 100° C. Then, a concentrated sulfuric acid solution (100 ml) containing 64.0 g (630 mmol) of potassium nitrate was slowly added dropwise and stirred for 1 hour while heating. After reaction, the solution was cooled to room temperature, poured into crushed ice, and filtered. Thus, a solid of 4,4'-dinitro-2,2'-bipyridyl-N,N'-oxide was obtained. Next, 7.0 g (25 mM) of 4,4'-dinitro-2,2'-bipyridyl-N,N'-oxide and 6.0 g of 10% palladium carbon were suspended in ethanol (23 ml) under an argon stream. To this solution was added dropwise an ethanol solution (47 ml) containing 6.3 g (126 mmol) of hydrazine monohydrate, followed by refluxing for 8 hours. The resultant solution was cooled and filtered. The filtrate was concentrated and purified by silica gel column chromatography. Thus, 4,4'-diamino-2, 2'-bipyridyl was obtained.

Synthesis

Ethylene glycol (10 mL) was placed in a 50 mL two-neck flask, in which DA-bpy (0.2 g) and RuCl$_3$ (0.1 g) were dissolved successively with stirring. The solution was heated by a mantle heater while vigorously stirring under a N$_2$ stream, followed by refluxing for about 4 hours.

Purification

After stirring under a N$_2$ stream and cooling, the solution was transferred to a 100 mL eggplant-shaped flask and washed with acetone (5 mL)+diethyl ether (20 mL). This washing of the solution with acetone (5 mL)+diethyl ether (20 mL) was repeated until the solvent (ethylene glycol) was removed sufficiently. The target substance thus washed was dissolved in ethanol and precipitated by the addition of diethyl ether. The target substance was filtered while washing with diethyl ether and dried under reduced pressure. Thus, a solid of [Ru(4,4'-diamino-2,2'-bipyridyl)$_3$] was obtained. This solid was dissolved in water to obtain a complex solution.

Example 9

Two types of osmium complexes were prepared in the following manner.

[OsCl(Him)(dmbpy)$_2$]

Synthesis

First, 2.00 g (4.56 mmol) of (NH$_4$)$_2$[OsCl$_6$] (manufactured by Aldrich) and 1.68 g (9.11 mmol) of 4,4'-dimethyl-2,2'-bipyridyl (dmbpy, manufactured by Wako Pure Chemical Industries, Ltd.) were refluxed in ethylene glycol (60 ml) for 1 hour under a nitrogen stream. After cooling to room temperature, 1M sodium hydrosulfite solution (120 ml) was added for 30 minutes, followed by cooling in an ice bath for 30 minutes. The precipitates thus produced were filtered under reduced pressure and sufficiently washed with water (500 to 1000 ml). Further, the precipitates were washed two times with diethyl ether, and then dried under reduced pressure. Thus, 1.5 to 1.7 g of [OsCl$_2$(dmbpy)$_2$] was obtained.

Next, 1.56 g (2.60 mmol) of the resultant [OsCl$_2$(dmbpy)$_2$] and 0.36 g (5.2 mmol) of imidazole (Him) were refluxed in a water/methanol mixed solvent (50 ml) for 2 hours under a nitrogen stream. After cooling to room temperature, a saturated NaCl solution (300 ml) was added. The precipitates thus produced were filtered under reduced pressure, washed with a saturated NaCl solution, and dried under reduced pressure. Thus, [OsCl(Him)(dmbpy)$_2$]Cl$_2$ was obtained.

Purification

The [OsCl(Him)(dmbpy)$_2$]Cl$_2$ was dissolved in the smallest possible amount of acetonitrile/methanol (1:1 v/v) and purified by column chromatography (an absorbent: activated alumina, a developing solvent: acetonitrile/methanol). The solvent was evaporated, the residue was dissolved in a small amount of acetone, and reprecipitated with diethyl ether. The precipitates thus produced were filtered and dried under reduced pressure, and then dissolved in water. Thus, a complex solution was obtained.

[Os(Him)$_2$(dmbpy)$_2$]

Synthesis

First, 2.00 g (4.56 mmol) of (NH$_4$)$_2$[OsCl$_6$] and 1.68 g (9.11 mmol) of dmbpy were refluxed in ethylene glycol (60 ml) for 1 hour under a nitrogen stream. After cooling to room temperature, 1M sodium hydrosulfite solution (120 ml) was added for 30 minutes, followed by cooling in an ice bath for 30 minutes. The precipitates thus produced were filtered under reduced pressure and sufficiently washed with water (500 to 1000 ml). Further, the precipitates were washed two times with diethyl ether, and then dried under reduced pressure. Thus, 1.5 to 1.7 g of [OsCl$_2$(dmbpy)$_2$] was obtained. Next, 1.56 g (2.60 mmol) of the resultant [OsCl$_2$(dmbpy)$_2$] and 0.36 g (5.2 mmol) of imidazole (Him) were refluxed in a 1,2-ethanedithiol solvent (50 ml) for 2 hours under a nitrogen stream. After cooling to room temperature, a saturated NaCl solution (300 ml) was added. The precipitates thus produced were filtered under reduced pressure, washed with a saturated NaCl solution, and dried under reduced pressure. Thus, [Os(Him)$_2$(dmbpy)$_2$]Cl$_2$ was obtained.

Purification

The [Os(Him)$_2$(dmbpy)$_2$]Cl$_2$ was dissolved in the smallest possible amount of acetonitrile/methanol (1:1 v/v) and purified by column chromatography (an absorbent: activated alumina, a developing solvent: acetonitrile/methanol). The solvent was evaporated, the residue was dissolved in a small amount of acetone, and reprecipitated with diethyl ether. The precipitates thus produced were filtered and dried under reduced pressure, and then dissolved in water. Thus, a complex solution was obtained.

Example 10

Figure 5:
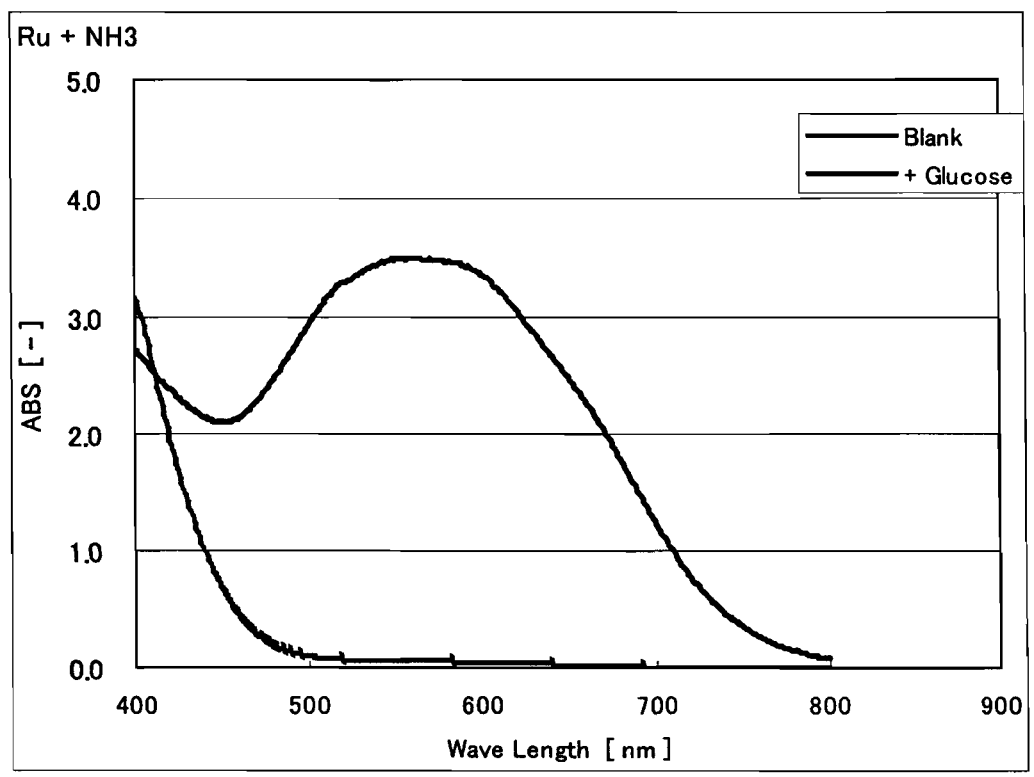
FIG. 5 is a graph showing coloring produced in a coloring reagent of still another example of the present invention.

A reagent solution was prepared by mixing a complex, an enzyme, a coloring reagent, and a buffer solution with the following composition. The complex was the same as that synthesized in the above examples. This is true for the following examples. The spectrum of the reagent solution was measured and identified as a blank. Further, glucose equivalent in amount to the complex was added to the reagent solution, and the spectrum was measured after the color change. FIG. 5 shows the results. The graph indicates the spectrum peculiar to a reduced WST-5 because the metal complex acted as an electron transfer agent to reduce WST-5.

Reagent Solution Composition

| PQQ-GDH | 50 U/mL |
|---|---|
| [Ru(NH$_3$)$_6$] | 0.8 mM |
| WST-5 | 0.2 mM |
| PIPES (pH 7) | 50 mM |
| Triton X-100 | 0.5% |

Example 11

Figure 6A:
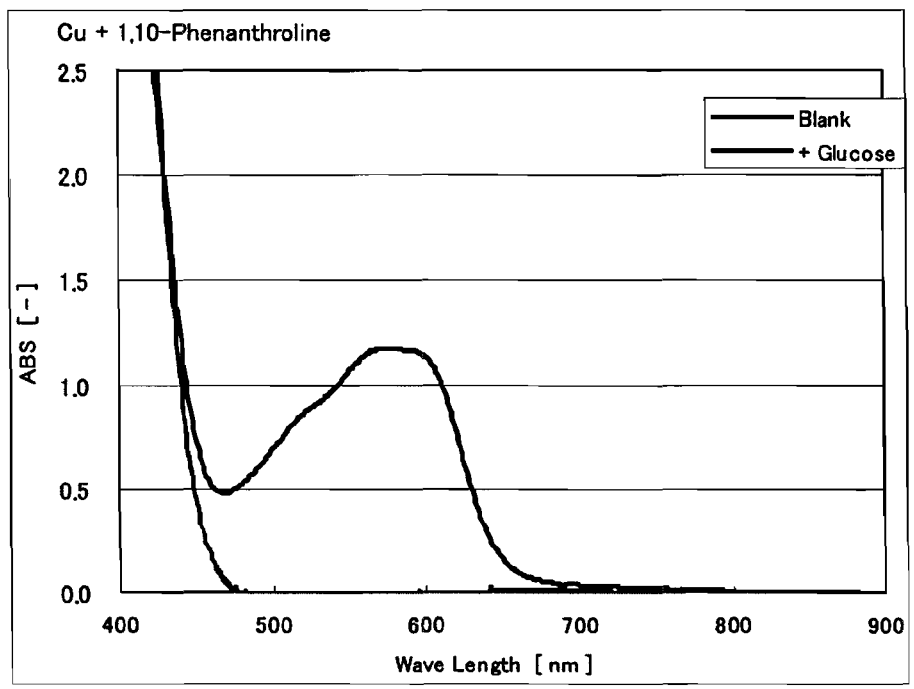
FIGS. 6A and 6B are graphs showing coloring produced in a coloring reagent of still another example of the present invention.
Figure 6B:
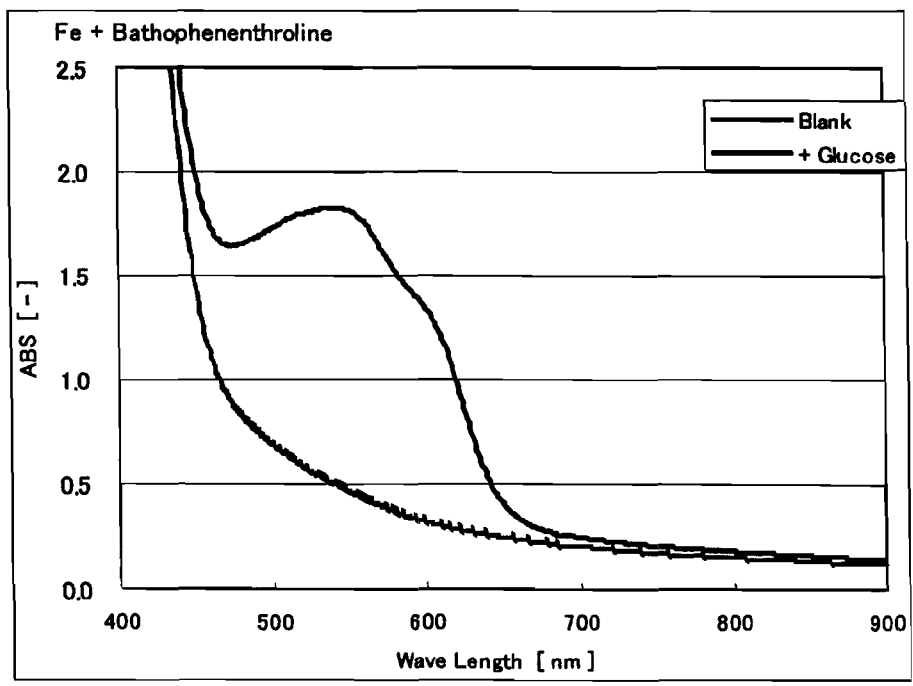

Reagent solutions were prepared by mixing a complex, an enzyme, a coloring reagent, and a buffer solution with the following compositions. The spectrum of each of the reagent solutions was measured and identified as a blank. Further, glucose equivalent in amount to the complex was added to each of the reagent solutions, and the spectrum was measured after the color change. FIGS. 6A and 6B show the results. Both graphs indicate the spectrum peculiar to a reduced MTT because the metal complex acted as an electron transfer agent to reduce MTT.

Reagent Solution Composition 1 (FIG. 6A)

| PQQ-GDH | 50 U/mL |
|---|---|
| [Cu(1,10-phenanthroline)$_2$] | 1 mM |
| MTT | 1 mM |
| PIPES (pH 7) | 50 mM |
| Triton X-100 | 0.5% |

Reagent Solution Composition 2 (FIG. 6B)

| PQQ-GDH | 50 U/mL |
|---|---|
| [Fe(bathophenanthroline)$_3$] | 1 mM |
| MTT | 1 mM |
| PIPES (pH 7) | 50 mM |
| Triton X-100 | 0.5% |

(bathophenanthroline = 4,7-diphenyl phenanthoroline)

Example 12

Figure 7A:
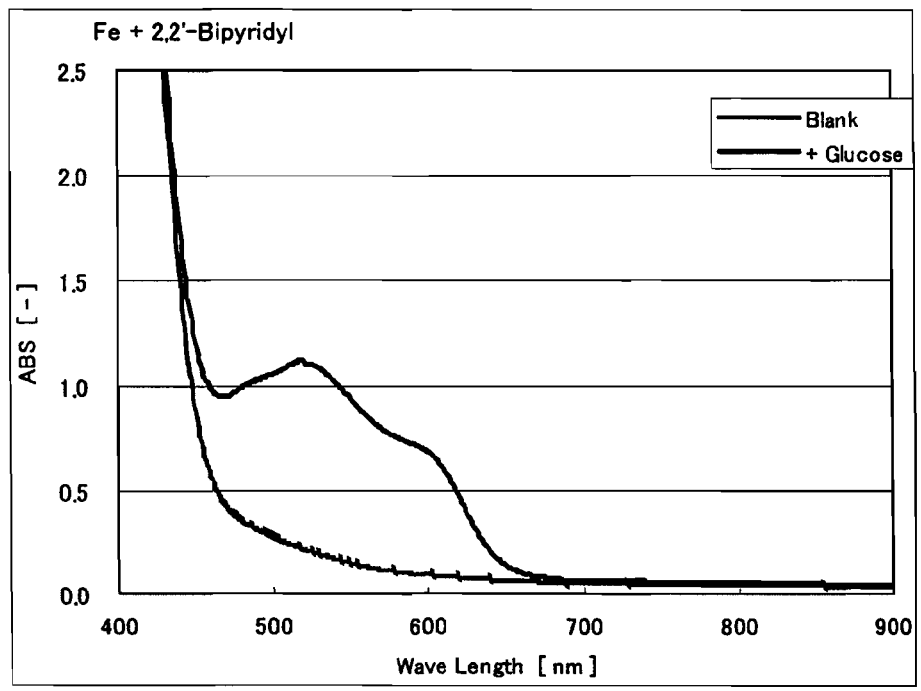
FIGS. 7A and 7B are graphs showing coloring produced in a coloring reagent of still another example of the present invention.
Figure 7B:
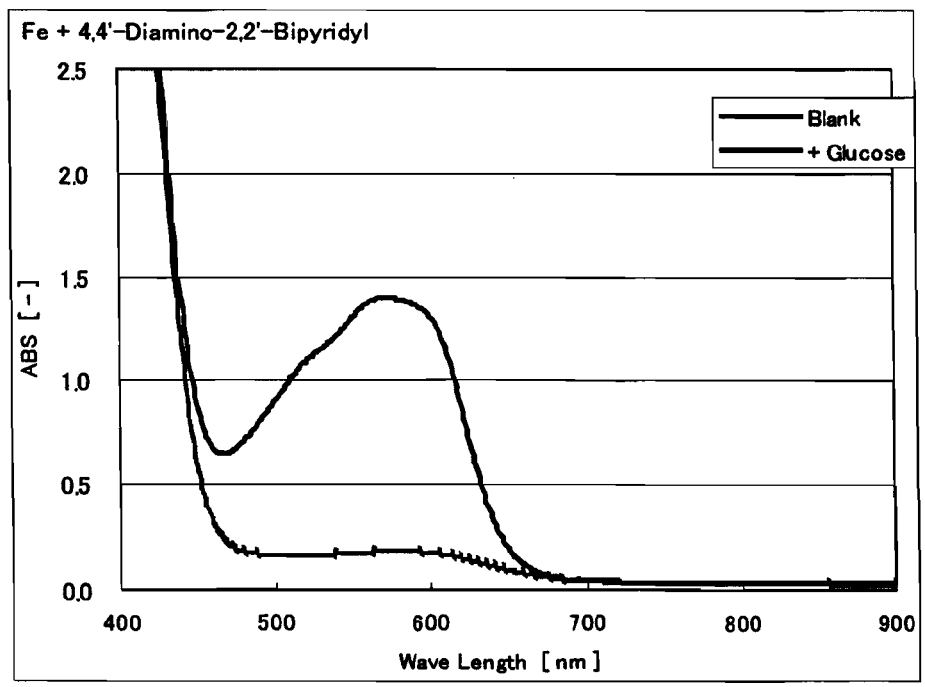

Reagent solutions were prepared by mixing a complex, an enzyme, a coloring reagent, and a buffer solution with the following compositions. The spectrum of each of the reagent solutions was measured and identified as a blank. Further, glucose equivalent in amount to the complex was added to each of the reagent solutions, and the spectrum was measured after the color change. FIGS. 7A and 7B show the results. Both graphs indicate the spectrum peculiar to a reduced MTT because the metal complex acted as an electron transfer agent to reduce MTT.

Reagent Solution Composition 1 (FIG. 7A)

| PQQ-GDH | 50 U/mL |
|---|---|
| [Fe(2,2'-bipyridyl)$_3$] | 1 mM |
| MTT | 1 mM |

| PIPES (pH 7) | 50 mM |
|---|---|
| Triton X-100 | 0.5% |

Reagent Solution Composition 2 (FIG. 7B)

| PQQ-GDH | 50 U/mL |
|---|---|
| [Fe(4,4'-diamino-2,2'-bipyridyl)$_3$] | 0.1 mM |
| MTT | 1 mM |
| PIPES (pH 7) | 50 mM |
| Triton X-100 | 0.5% |

Example 13

Figure 8:
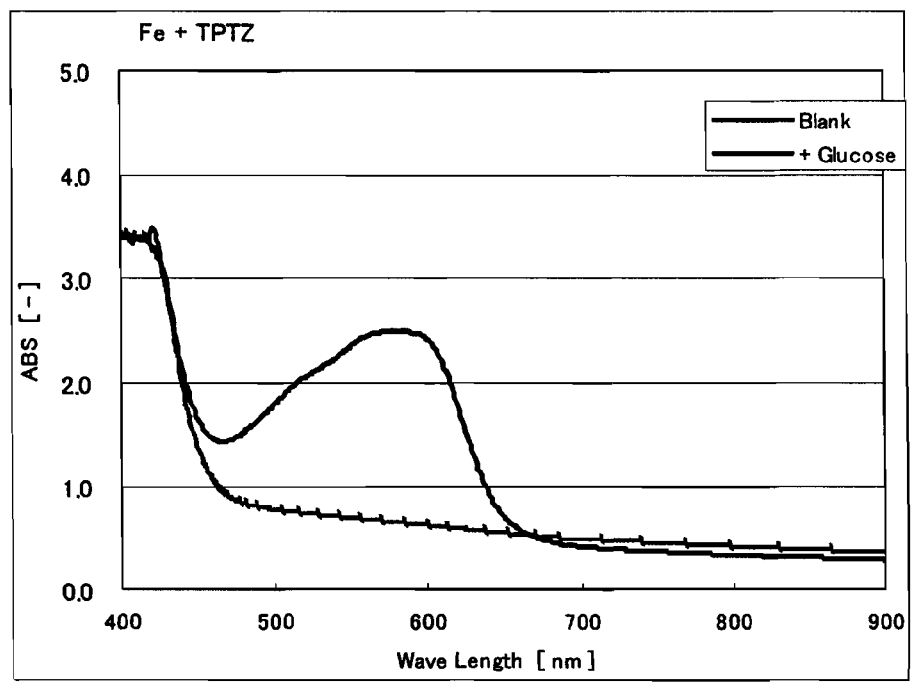
FIG. 8 is a graph showing coloring produced in a coloring reagent of still another example of the present invention.

A reagent solution was prepared by mixing a complex, an enzyme, a coloring reagent, and a buffer solution with the following composition. The spectrum of the reagent solution was measured and identified as a blank. Further, glucose equivalent in amount to the complex was added to the reagent solution, and the spectrum was measured after the color change. FIG. 8 shows the results. The graph indicates the spectrum peculiar to a reduced MTT because the metal complex acted as an electron transfer agent to reduce MTT.
Reagent Solution Composition

| PQQ-GDH | 50 U/mL |
|---|---|
| [Fe(TPTZ)$_3$] | 0.1 mM |
| MTT | 1 mM |
| PIPES (pH 7) | 50 mM |
| Triton X-100 | 0.5% |

(TPTZ = 2,4,6-tripyridyl-s-triazine)

Example 14

Figure 9:
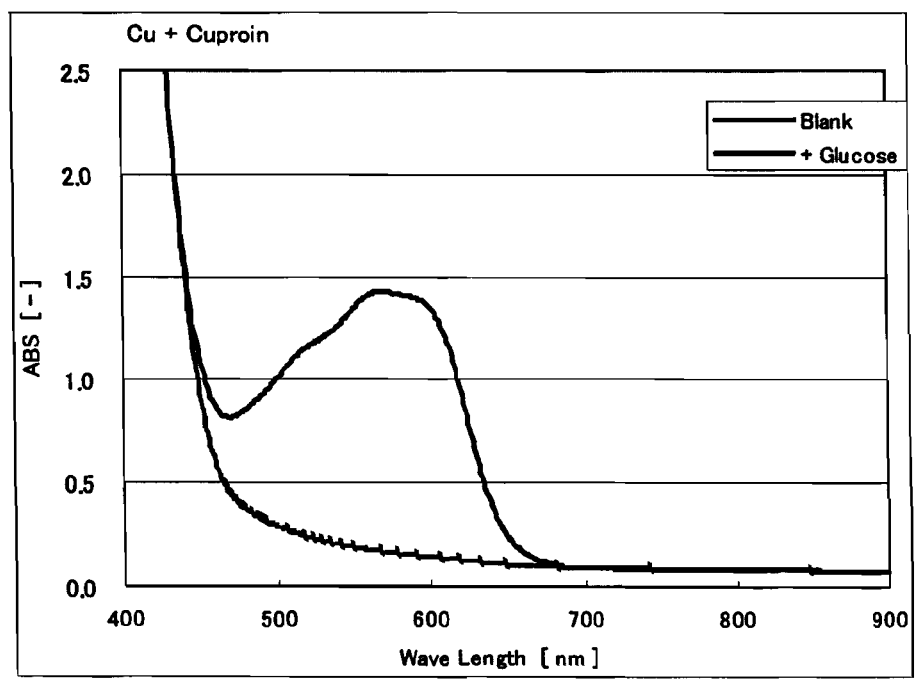
FIG. 9 is a graph showing coloring produced in a coloring reagent of still another example of the present invention.

A reagent solution was prepared by mixing a complex, an enzyme, a coloring reagent, and a buffer solution with the following composition. The spectrum of the reagent solution was measured and identified as a blank. Further, glucose equivalent in amount to the complex was added to the reagent solution, and the spectrum was measured after the color change. FIG. 9 shows the results. The graph indicates the spectrum peculiar to a reduced MTT because the metal complex acted as an electron transfer agent to reduce MTT.
Reagent Solution Composition

| PQQ-GDH | 50 U/mL |
|---|---|
| [Cu(Cuproin)$_2$] | 1 mM |
| MTT | 1 mM |
| PIPES (pH 7) | 50 mM |
| Triton X-100 | 0.5% |

(Cuproin = 2,2'-biquinoline)

Example 15

Figure 10:
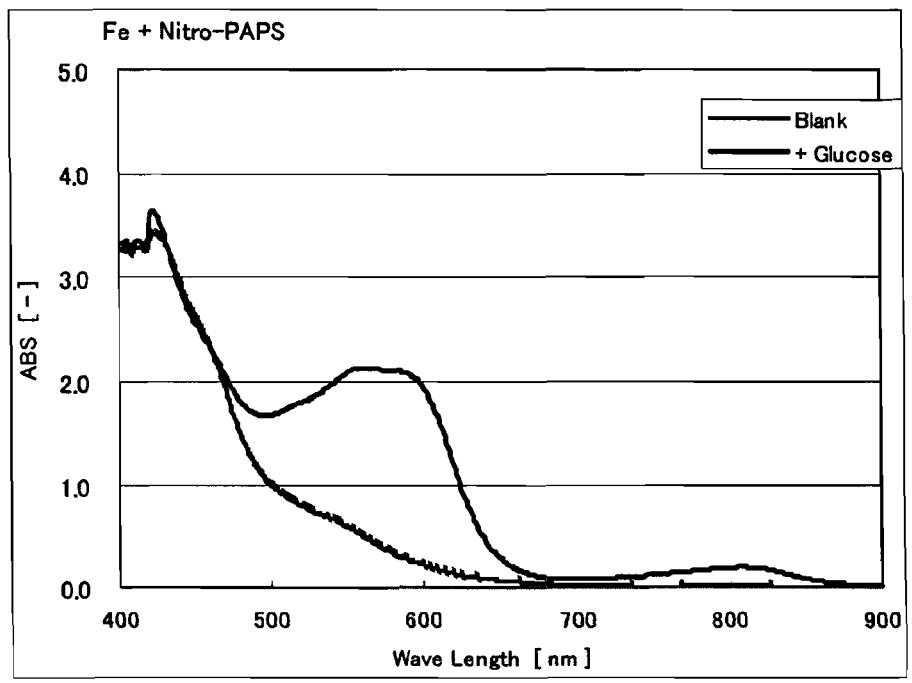
FIG. 10 is a graph showing coloring produced in a coloring reagent of still another example of the present invention.

A reagent solution was prepared by mixing a complex, an enzyme, a coloring reagent, and a buffer solution with the following composition. The spectrum of the reagent solution was measured and identified as a blank. Further, glucose equivalent in amount to the complex was added to the reagent solution, and the spectrum was measured after the color change. FIG. 10 shows the results. The graph indicates the spectrum peculiar to a reduced MTT because the metal complex acted as an electron transfer agent to reduce MTT.
Reagent Solution Composition

| PQQ-GDH | 50 U/mL |
|---|---|
| [Fe(nitro-PAPS)$_3$] | 0.02 mM |
| MTT | 1 mM |
| PIPES (pH 7) | 50 mM |
| Triton X-100 | 0.5% |

Example 16

Figure 11:
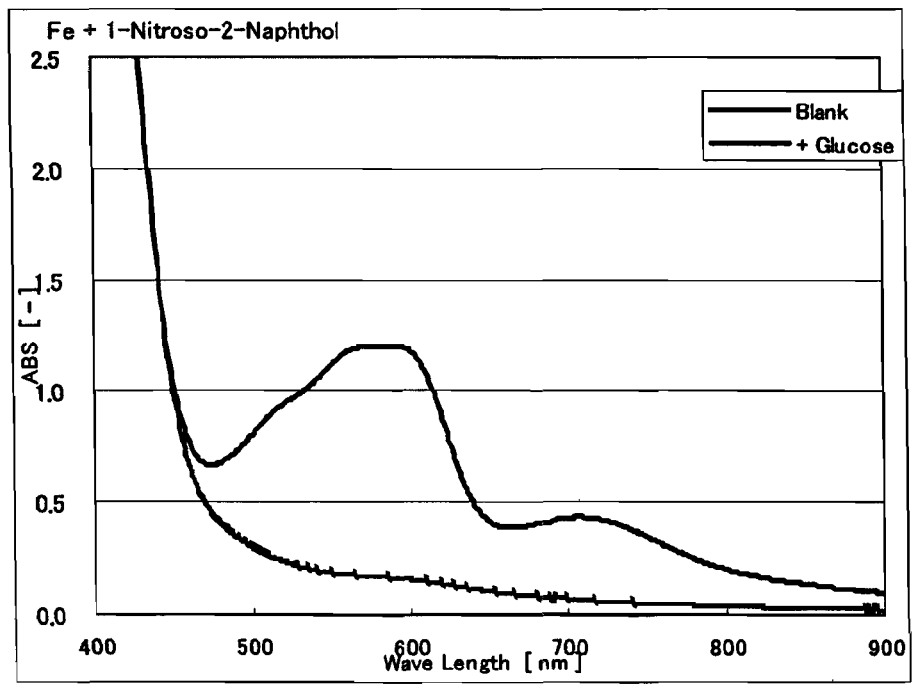
FIG. 11 is a graph showing coloring produced in a coloring reagent of still another example of the present invention.

A reagent solution was prepared by mixing a complex, an enzyme, a coloring reagent, and a buffer solution with the following composition. The spectrum of the reagent solution was measured and identified as a blank. Further, glucose equivalent in amount to the complex was added to the reagent solution, and the spectrum was measured after the color change. FIG. 11 shows the results. The graph indicates the spectrum peculiar to a reduced MTT because the metal complex acted as an electron transfer agent to reduce MTT.
Reagent Solution Composition

| PQQ-GDH | 50 U/mL |
|---|---|
| [Fe(1-nitroso-2-naphthol)$_3$] | 0.1 mM |
| MTT | 1 mM |
| PIPES (pH 7) | 50 mM |
| Triton X-100 | 0.5% |

Example 17

Figure 12:
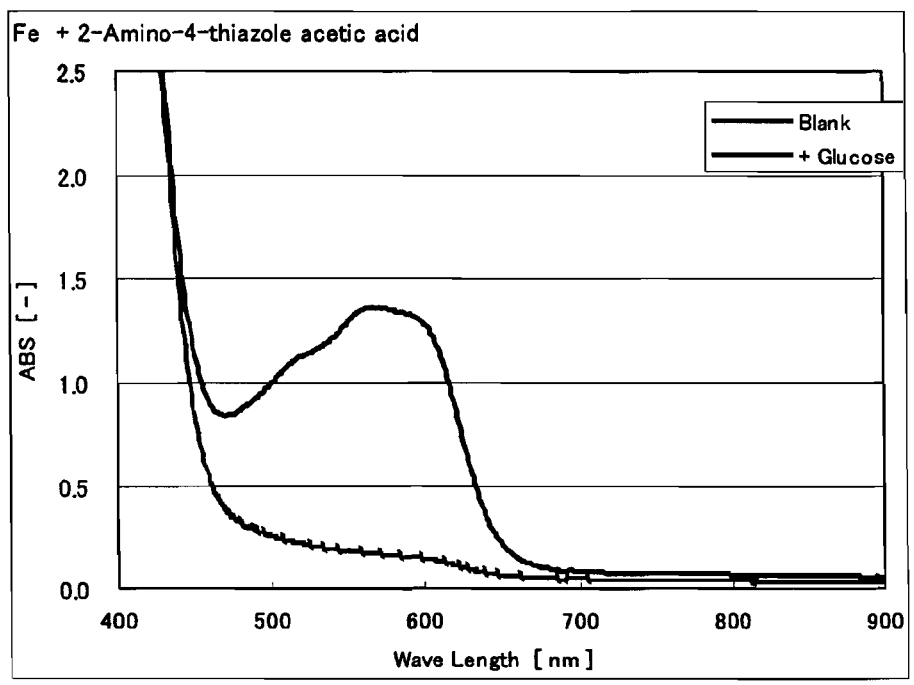
FIG. 12 is a graph showing coloring produced in a coloring reagent of still another example of the present invention.

A reagent solution was prepared by mixing a complex, an enzyme, a coloring reagent, and a buffer solution with the following composition. The spectrum of the reagent solution was measured and identified as a blank. Further, glucose equivalent in amount to the complex was added to the reagent solution, and the spectrum was measured after the color change. FIG. 12 shows the results. The graph indicates the spectrum peculiar to a reduced MTT because the metal complex acted as an electron transfer agent to reduce MTT.
Reagent Solution Composition

| PQQ-GDH | 50 U/mL |
|---|---|
| [Fe(2-amino-4-thiazoleacetic acid)$_3$] | 1 mM |
| MTT | 1 mM |
| PIPES (pH 7) | 50 mM |
| Triton X-100 | 0.5% |

Example 18

Figure 13:
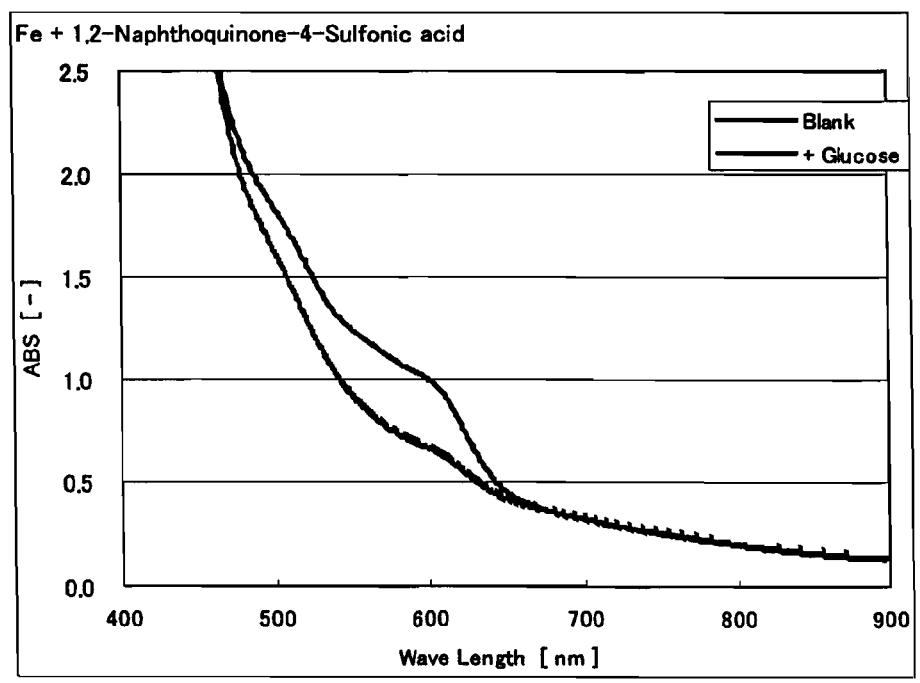
FIG. 13 is a graph showing coloring produced in a coloring reagent of still another example of the present invention.

A reagent solution was prepared by mixing a complex, an enzyme, a coloring reagent, and a buffer solution with the following composition. The spectrum of the reagent solution was measured and identified as a blank. Further, glucose equivalent in amount to the complex was added to the reagent solution, and the spectrum was measured after the color change. FIG. 13 shows the results. The graph indicates the spectrum peculiar to a reduced MTT because the metal complex acted as an electron transfer agent to reduce MTT.

Reagent Solution Composition

| | |
|---|---|
| PQQ-GDH | 50 U/mL |
| [Fe(1,2-naphthoquinone-4-sulfonic acid)$_3$] | 1 mM |
| MTT | 1 mM |
| PIPES (pH 7) | 50 mM |
| Triton X-100 | 0.5% |

Example 19

Figure 14A:
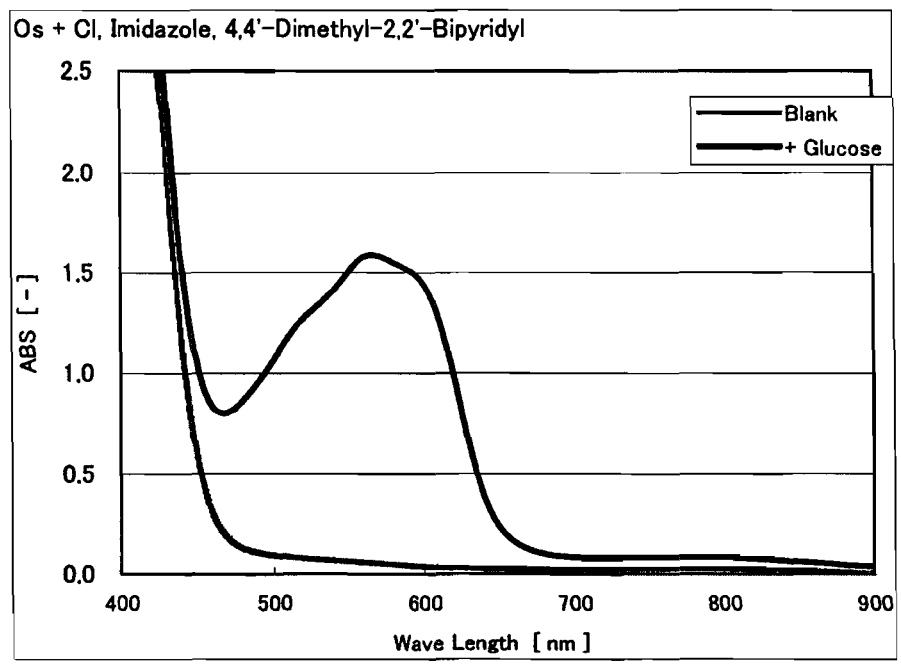
FIGS. 14A and 14B are graphs showing coloring produced in a coloring reagent of still another example of the present invention.
Figure 14B:
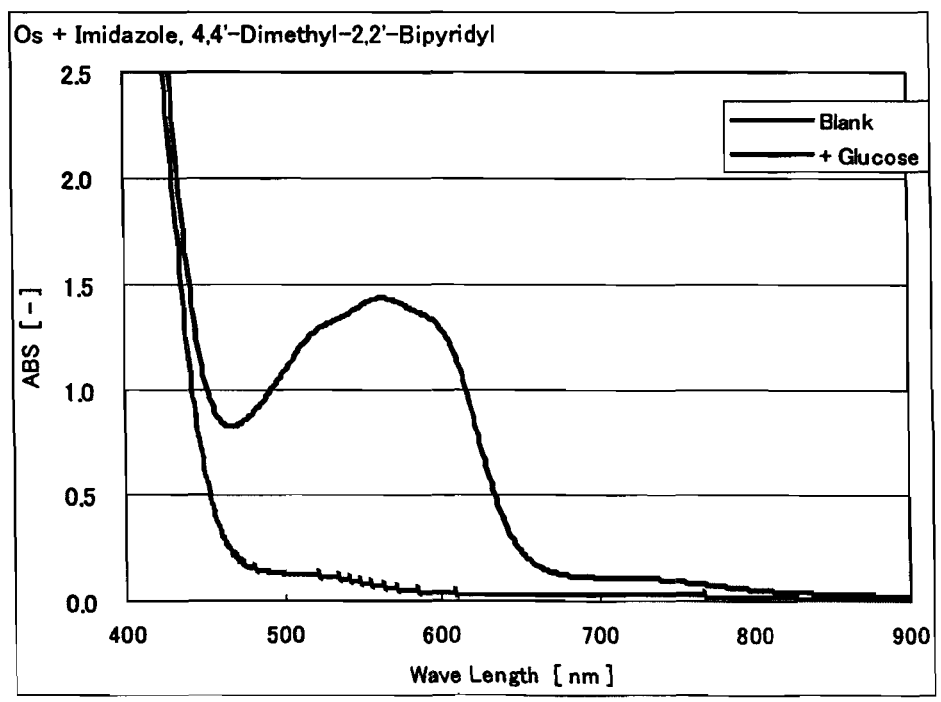

Reagent solutions were prepared by mixing a complex, an enzyme, a coloring reagent, and a buffer solution with the following compositions 1, 2. The spectrum of each of the reagent solutions was measured and identified as a blank. Further, glucose equivalent in amount to the complex was added to each of the reagent solutions, and the spectrum was measured after the color change. FIGS. 14A and 14B show the results. Both graphs indicate the spectrum peculiar to a reduced MTT because the metal complex acted as an electron transfer agent to reduce MTT.

Reagent Solution Composition 1 (FIG. 14A)

| | |
|---|---|
| PQQ-GDH | 50 U/mL |
| [OsCl(Him)(dmbpy)$_2$] | 0.1 mM |
| MTT | 1 mM |
| PIPES (pH 7) | 50 mM |
| Triton X-100 | 0.5% |

(Him = imidazole)
(dmbpy = 4,4'-dimethyl-2,2'-bipyridyl)

Reagent Solution Composition 2 (FIG. 14B)

| | |
|---|---|
| PQQ-GDH | 50 U/mL |
| [Os(Him)$_2$(dmbpy)$_2$] | 0.1 mM |
| MTT | 1 mM |
| PIPES (pH 7) | 50 mM |
| Triton X-100 | 0.5% |

(Him = imidazole)
(dmbpy = 4,4'-dimethyl-2,2'-bipyridyl)

Example 20

Figure 15:
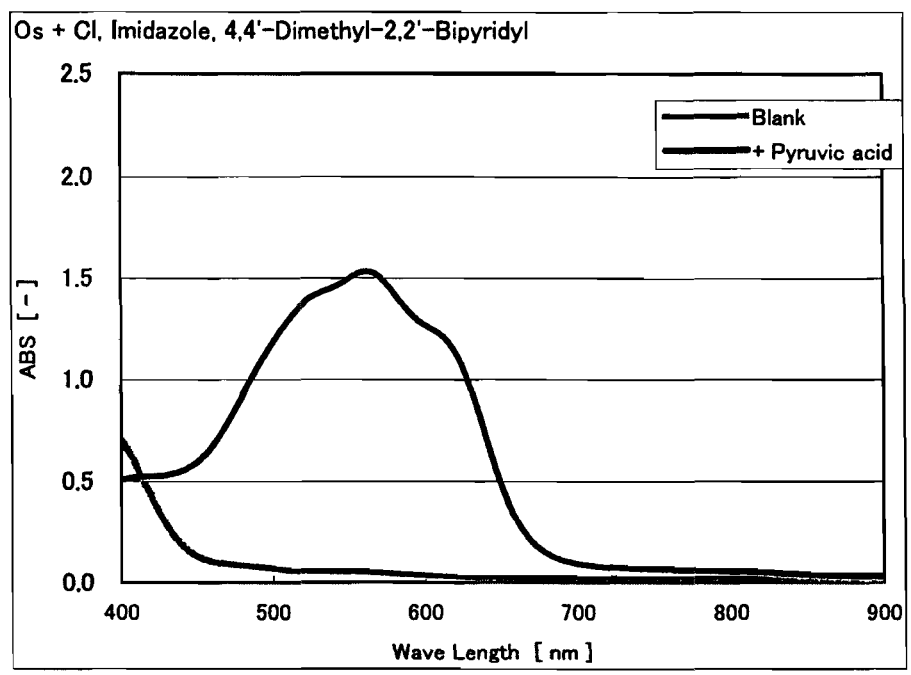
FIG. 15 is a graph showing coloring produced in a coloring reagent of still another example of the present invention.

A reagent solution was prepared by mixing a complex, an enzyme (pyruvate oxidase), a coloring reagent, and a buffer solution with the following composition. The spectrum of the reagent solution was measured and identified as a blank. Further, glucose equivalent in amount to the complex was added to the reagent solution, and the spectrum was measured after the color change. FIG. 15 shows the results. The graph indicates the spectrum peculiar to a reduced MTT because the metal complex acted as an electron transfer agent to reduce MTT.

Reagent Solution Composition

| | |
|---|---|
| Pyruvate oxidase | 100 U/mL |
| [OsCl(Him)(dmbpy)$_2$] | 0.2 mM |
| MTT | 1 mM |
| PIPES (pH 7) | 50 mM |
| Triton X-100 | 0.5% |

(Him = imidazole)
(dmbpy = 4,4'-dimethyl-2,2'-bipyridyl)

Example 21

Figure 16A:
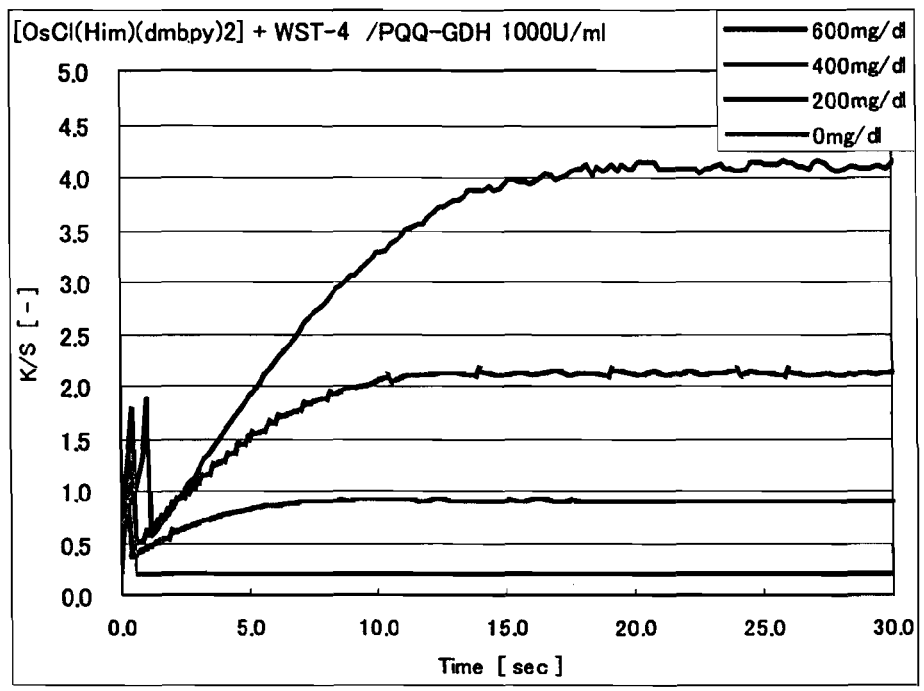
FIGS. 16A and 16B are graphs showing coloring produced in a coloring reagent of still another example of the present invention.
Figure 16B:
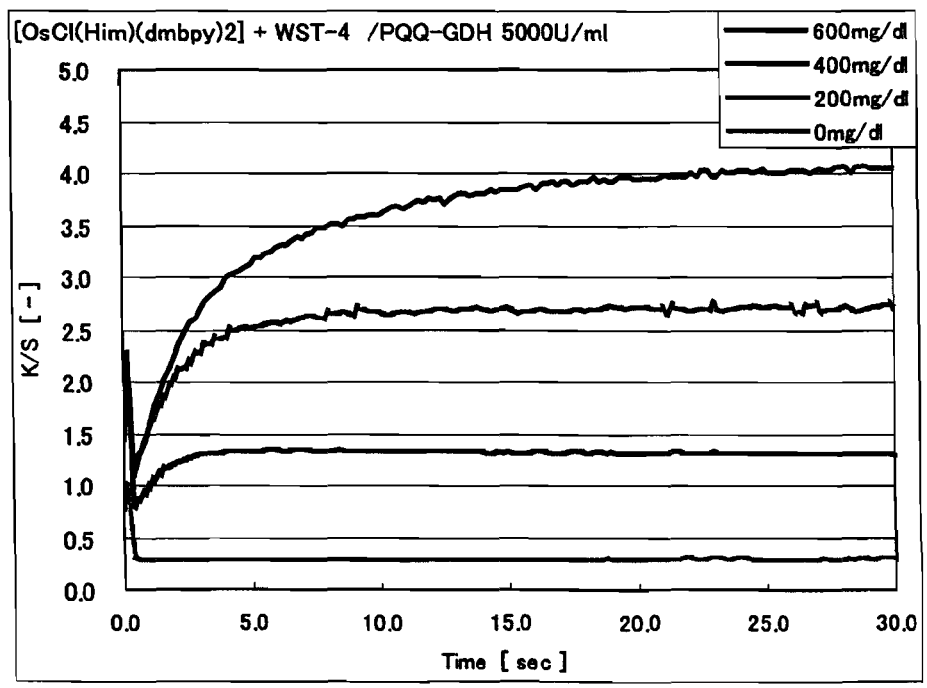

This example proved that the reaction rate of a reagent can be improved by increasing the amount of enzyme. Two mesh fabrics (10 cm×10 cm) were impregnated respectively with reagent solutions (1 ml) having the following compositions 1, 2 and dried with hot air. These fabrics were attached to polyethylene terephthalate (PET) films and cut into a predetermined shape, thus producing two test pieces with different amounts of enzyme. Serum-based glucose reference solutions (0, 200, 400, 600 mg/dl) were used as samples, and each of the samples was dropped on the test pieces to observe a K/S change for 30 seconds with a reflectance measuring device (LED/wavelength 660 nm). The serum-based glucose reference solutions were prepared in the following manner. Human blood plasma was glycolyzed completely, frozen and melted to produce serum. Then, a glucose solution was added to this serum. FIGS. 16A and 16B show the results. As shown in the graphs, the reagent solution including 5000 U/ml of enzyme improves the reaction rate compared with the reagent solution including 1000 U/ml of enzyme, and the reaction comes to an end in about 5 seconds. Sampling the signals near 5 seconds, at which the reaction seems to reach the end, makes it possible to quantify the glucose. The slope of the graph from the beginning to the end of the reaction also can be used to quantify the glucose.

Reagent Solution Composition 1 (FIG. 16A)

| | |
|---|---|
| PQQ-GDH | 1000 U/mL |
| [OsCl(Him)(dmbpy)$_2$] | 1 mM |
| MTT | 30 mM |
| PIPES (pH 6.5) | 80 mM |
| MEGA-8 (DOJINDO LABORATORIES) | 1% |
| Polyacrylamide | 0.1% |
| BSA | 1% |

Reagent Solution Composition 2 (FIG. 16B)

| | |
|---|---|
| PQQ-GDH | 5000 U/ml |
| [OsCl(Him)(dmbpy)$_2$] | 1 ml |
| MTT | 30 mM |
| PIPES (pH 6.5) | 80 mM |
| MEGA-8 (DOJINDO LABORATORIES) | 1% |
| Polyacrylamide | 0.1% |
| BSA | 1% |

INDUSTRIAL APPLICABILITY

As described above, a calorimetric method of the present invention can perform simple and reliable analysis in a short time.

The invention claimed is:
1. A reagent useful for a colorimetric method comprising:
transferring an electron from an analyte to a coloring reagent that produces color by reduction via a mediator by using an oxidoreductase; and performing qualitative or quantitative analysis of the analyte by measuring color produced in the coloring reagent, and;

the reagent comprising:
an oxidoreductase;
a mediator; and
a coloring reagent for producing color by reduction,
wherein the mediator is at least one selected from the group consisting of a copper complex, an iron complex, an osmium complex, and a ruthenium complex,
wherein iron complex has a at least one ligand selected from the group consisting of ammonia, an imidazole compound, a phenanthroline compound, a triazine compound, a biquinoline compound, a pyridylazo compound, a nitroso compound, an oxine compound, a benzothiazole compound, and a derivative of each of the compounds, or the iron complex is selected from the group consisting of Fe(4,4'-dimethyl-2,2'-bipyridyl)$_3$, Fe(4,4'-diphenyl-2,2'-bipyridyl)$_3$, Fe(4,4'-diamino-2,2'-bipyridyl)$_3$, Fe(4,4'-dihydroxy-2,2'-bipyridyl)$_3$, Fe(4,4'-dicarboxy-2,2'-bipyridyl)$_3$, Fe(4,4'-dibromo-2,2'-bipyridyl)$_3$, Fe(5,5'-dimethyl-2,2'-bipyridyl)$_3$, Fe(5,5'-diphenyl-2,2'-bipyridyl)$_3$, Fe(5,5'-diamino-2,2'-bipyridyl)$_3$, Fe(5 5'-dihydroxy-2,2'-bipyridyl)$_3$, Fe(5,5'-dicarboxy-2,2'-bipyridyl)$_3$, and Fe(5,5'-dibromo-2,2'-bipyridyl)$_3$, and
wherein the copper complex, the osmium complex, and the ruthenium complex have at least one ligand selected from the group consisting of ammonia, a bipyridyl compound, an imidazole compound, a phenanthroline compound, a triazine compound, a biquinoline compound, a pyridylazo compound, a nitroso compound, an oxine compound, a benzothiazole compound, and a derivative of each of the compounds.

2. The reagent according to claim 1, wherein a coordinating atom of a ligand in the complex is at least one selected from the group consisting of nitrogen, oxygen, and sulfur.

3. The reagent according to claim 1, wherein at least one hydrogen atom that occupies a position other than a coordination position of the ligand is replaced by a substituent.

4. The reagent according to claim 3, wherein the substituent is at least one selected from the group consisting of an alkyl group, an aryl group, an allyl group, a phenyl group, a hydroxyl group, an alkoxy group, a carboxy group, a carbonyl group, a sulfone group, a sulfonyl group, a nitro group, a nitroso group, a primary amine, a secondary amine, a tertiary amine, an amino group, an acyl group, an amido group, and a halogen group.

5. The reagent according to claim 1, wherein the complex includes at least two or more types of ligands.

6. The reagent according to claim 1, wherein the oxidoreductase is a dehydrogenase or an oxidase.

7. The reagent according to claim 1, wherein the coloring reagent is a tetrazolium salt.

8. The reagent according to claim 7, wherein the tetrazolium salt has at least one group selected from a nitrophenyl group, a thiazolyl group, and a benzothiazolyl group.

9. The reagent according to claim 7, wherein the tetrazolium salt is at least one coloring reagent selected from the group consisting of MTT, INT, Neo-TB, Nitro-TB, TB, WST-1, WST-3, WST-4, WST-5, WST-8, 2-(2-benzothiazolyl)-3,5-diphenyltetrazolium bromide, 2-(2-benzothiazolyl)-3-(4-nitrophenyl)-5-phenyltetrazolium bromide, 2,3-bis(4-nitrophenyl)-5-phenyltetrazolium chloride, 2,3-di(4-nitrophenyl)tetrazolium perchlorate, 3-(3-nitrophenyl)-5-methyl-2-phenyltetrazolium chloride, and 3-(4-nitrophenyl)-5-methyl-2-phenyltetrazolium chloride.

10. The reagent according to claim 1, wherein the analyte is glucose, cholesterol, uric acid, pyruvic acid, lactic acid, creatine, or creatinine, and the oxidoreductase is a dehydrogenase or an oxidase that corresponds to each of the analytes.

11. A test piece for colorimetric analysis comprising the reagent according to claim 1.

12. The test piece according to claim 11, further comprising an inorganic gel.

* * * * *